United States Patent
Guo et al.

(10) Patent No.: US 11,759,143 B2
(45) Date of Patent: Sep. 19, 2023

(54) SKIN DETECTION METHOD AND ELECTRONIC DEVICE

(71) Applicant: HONOR DEVICE CO., LTD., Guangdong (CN)

(72) Inventors: Zhizhi Guo, Guangdong (CN); Hongwei Hu, Guangdong (CN); Wenmei Gao, Guangdong (CN); Chen Dong, Guangdong (CN)

(73) Assignee: HONOR DEVICE CO., LTD., Guangdong (CN)

( * ) Notice: Subject to any disclaimer, the term of this patent is extended or adjusted under 35 U.S.C. 154(b) by 133 days.

(21) Appl. No.: 17/418,368

(22) PCT Filed: Dec. 2, 2019

(86) PCT No.: PCT/CN2019/122317
§ 371 (c)(1),
(2) Date: Jun. 25, 2021

(87) PCT Pub. No.: WO2020/134877
PCT Pub. Date: Jul. 2, 2020

(65) Prior Publication Data
US 2022/0148161 A1    May 12, 2022

(30) Foreign Application Priority Data
Dec. 26, 2018  (CN) .......................... 201811603196.8

(51) Int. Cl.
*G06T 7/90* (2017.01)
*G06T 11/00* (2006.01)
(Continued)

(52) U.S. Cl.
CPC ............ *A61B 5/441* (2013.01); *A61B 5/1032* (2013.01); *A61B 5/444* (2013.01); *A61B 5/7435* (2013.01);
(Continued)

(58) Field of Classification Search
CPC .... G06V 10/25; G06V 40/171; G06V 40/166; G06V 40/16; G06V 10/56; G06V 10/507;
(Continued)

(56) References Cited

U.S. PATENT DOCUMENTS 5,938,593 A * 8/1999 Ouellette ............. A61B 5/7435
324/692
6,571,003 B1   5/2003 Hillebrand et al.
(Continued)

FOREIGN PATENT DOCUMENTS

CN      1781448 A  *  6/2000  ............. A61B 5/442
CN      1781448 A     6/2006
(Continued)

OTHER PUBLICATIONS

Foreign Communication From a Counterpart Application, PCT Application No. PCT/CN2019/122317, English Translation of International Search Report dated Mar. 6, 2020, 3 pages.
(Continued)

*Primary Examiner* — Wesner Sajous

(57) ABSTRACT

A skin detection and evaluation method includes: obtaining a face image of a user; detecting a skin problem that appears in the face image; prompting in a first interface, the user that the skin problem appears on a face, wherein the first interface comprises the face image; and displaying a second interface in response to a first operation performed by the user in the first interface, wherein the second interface comprises a first facial simulated image obtained after the skin problem is aged; or displaying a third interface in response to a second operation performed by the user in the first interface, wherein the third interface comprises a second facial simulated image obtained after the skin problem is de-aged.

10 Claims, 27 Drawing Sheets

(51) Int. Cl.
| | |
|---|---|
| *G06T 7/00* | (2017.01) |
| *G06T 11/60* | (2006.01) |
| *G06F 3/048* | (2013.01) |
| *H04N 1/60* | (2006.01) |
| *A61B 5/00* | (2006.01) |
| *A61B 5/103* | (2006.01) |
| *G06F 3/04847* | (2022.01) |
| *G06V 10/56* | (2022.01) |
| *G06V 10/50* | (2022.01) |
| *G06V 40/16* | (2022.01) |

(52) U.S. Cl.
CPC ........ *G06F 3/04847* (2013.01); *G06T 7/0012* (2013.01); *G06T 7/90* (2017.01); *G06T 11/001* (2013.01); *G06T 11/60* (2013.01); *G06V 10/507* (2022.01); *G06V 10/56* (2022.01); *G06V 40/169* (2022.01); *G06V 40/171* (2022.01); *G06T 2200/24* (2013.01); *G06T 2207/30088* (2013.01); *G06T 2207/30201* (2013.01)

(58) Field of Classification Search
CPC .. G06V 40/169; G06V 2201/03; G06V 20/40; G06V 40/107; G06V 40/161; G06T 5/002; G06T 7/73; G06T 2207/30201; G06T 11/60; G06T 11/001; G06T 7/90; G06T 2207/30088; G06T 7/0012; G06T 2200/24; A61B 5/1032; A61B 5/7425; A61B 5/441; A61B 5/444; A61B 5/445; A61B 5/743; A61B 5/6898; A61B 5/442; A61B 5/7435; A61B 5/0022; A61B 5/0077; G06Q 10/109; G06Q 10/10; G06F 3/0481; G06F 3/04847; G06F 3/017; G16H 40/67; A45D 44/005; A45D 2044/007; G06N 3/063; H04N 1/60; H04N 5/57–5/58; H04N 1/58; H04N 1/6027; H04N 1/6075; H04N 1/6077; H04N 9/64; H04N 9/69; H04N 9/70; H04N 9/73; G09G 5/02; G09G 5/04; G09G 5/10; G09G 5/30; G09G 2320/02; G09G 2320/0242; G09G 2320/0233; G09G 2320/0606; G09G 2320/0666
USPC ........................................................ 345/589
See application file for complete search history.

(56) References Cited

U.S. PATENT DOCUMENTS

| | | | |
|---|---|---|---|
| 2008/0212894 A1* | 9/2008 | Demirli | G06T 11/00 382/276 |
| 2008/0273110 A1* | 11/2008 | Joza | H04N 5/235 348/E5.022 |
| 2014/0304629 A1 | 10/2014 | Cummins et al. | |
| 2018/0033205 A1* | 2/2018 | Kong | A61B 5/7275 |
| 2018/0276883 A1 | 9/2018 | D'Alessandro | |
| 2019/0125249 A1* | 5/2019 | Rattner | A61B 5/0077 |
| 2020/0170564 A1* | 6/2020 | Jiang | A61B 5/0077 |

FOREIGN PATENT DOCUMENTS

| | | |
|---|---|---|
| CN | 101652784 A | 2/2010 |
| CN | 101916370 A | 12/2010 |
| CN | 103152476 A | 6/2013 |
| CN | 103251406 A | 8/2013 |
| CN | 109793498 A | 5/2019 |
| EP | 3885968 A1 | 9/2021 |
| WO | 0076398 A1 | 12/2000 |

OTHER PUBLICATIONS

Foreign Communication From a Counterpart Application, European Patent Application No. 19902077.7, extended European search report dated Dec. 15, 2021, 11 pages.

Kamenicky Jan et al: "Contrast preserving color fusion", Proc. SPIE 7866, Color Imaging XVI: Displaying, Processing, Hardcopy, and Applications, Jan. 25, 2011 (Jan. 25, 2011), 8 pages.

* cited by examiner

SKIN DETECTION METHOD AND ELECTRONIC DEVICE

CROSS-REFERENCE TO RELATED APPLICATIONS

This application is a National Stage of International Application No. PCT/CN2019/122317, filed on Dec. 2, 2019, which claims priority to Chinese Patent Application No. 201811603196.8, filed on Dec. 26, 2018, both of which are hereby incorporated by reference in their entireties.

This application claims priority to Chinese Patent Application No. 201811603196.8, filed with the China National Intellectual Property Administration on Dec. 26, 2018 and entitled "SKIN DETECTION METHOD AND ELECTRONIC DEVICE", which is incorporated herein by reference in its entirety.

TECHNICAL FIELD

This application relates to the field of image processing technologies, and in particular, to a skin detection method and an electronic device.

BACKGROUND

Skin detection (skin test) means a scientific test of skin texture for purposes of skin protection and correct selection of a suitable skin care product. Generally, a user may use a professional optical device to detect items such as blackheads, spots, wrinkles, pores, oil distribution, and glossiness of the user's face, to learn about the user's skin health condition, and then set a skin care solution suitable for the user.

Currently, some application vendors have launched a detection application (APP) with a skin detection function. If the detection application is installed on a mobile terminal such as a mobile phone, a user may use the detection application to perform skin detection. For example, the detection application may collect image information of a user's face by using a camera of the mobile phone. Further, the mobile phone may analyze a skin problem such as spots or wrinkles on the user's face based on the collected image information by using a specific image processing algorithm. For these skin problems, the phone may further provide a skin care suggestion to the user. However, the user cannot intuitively understand a specific change caused by these skin problems to a face in a period of time, and consequently, a possibility of accepting, by the user, the skin care suggestion provided by the mobile phone is not high.

SUMMARY

This application provides a skin detection method and an electronic device, to actually simulate, for a detected skin problem, a change of the skin problem in a period of time, so that a user can intuitively sense a skin change, and therefore the user can be reminded to repair the skin problem in a timely manner.

To achieve the foregoing objectives, this application uses the following technical solutions:

According to a first aspect, this application provides a skin detection method, and includes: An electronic device obtains a face image of a user. The electronic device detects a skin problem that appears in the face image. The electronic device prompts, in a first interface, the user that the skin problem appears on a face, where the first interface includes the face image. If it is detected that the user performs a first operation in the first interface, the electronic device may display a second interface, where the second interface includes a first facial simulated image obtained after the skin problem is aged; or if it is detected that the user performs a second operation in the first interface, the electronic device may display a third interface, where the third interface includes a second facial simulated image obtained after the skin problem is de-aged.

It can be learned that the electronic device may simulate, for the detected skin problem (for example, a color spot problem or a fine line problem), a change in aging/de-aging of the skin problem in a period of time, and a mobile phone may display, to the user, the facial simulated image obtained after the aging/de-aging, so that the user can intuitively and vividly sense a possible change of the user's skin in a future period of time, and therefore the user can be reminded to repair the skin problem in a timely manner, thereby improving use experience of the user.

In a possible design method, the skin problem may specifically include a color spot problem. In this case, that the electronic device detects a skin problem that appears in the face image specifically includes: The electronic device detects, in the face image, a color spot region in which the color spot problem appears.

In a possible design method, before the electronic device displays the second interface in response to the first operation of the user in the first interface, the method further includes: The electronic device performs aging processing on the color spot region in the face image to obtain the first facial simulated image. Alternatively, before the electronic device displays the third interface in response to the second operation of the user in the first interface, the method further includes: The electronic device performs de-aging processing on the color spot region in the face image to obtain the second facial simulated image.

For example, that the electronic device performs aging processing on the color spot region in the face image to obtain the first facial simulated image specifically includes: The electronic device obtains a change coefficient K1 of an L pixel channel, a change coefficient K2 of an a pixel channel, and a change coefficient K3 of a b pixel channel in the color spot region. The electronic device performs aging processing on the L pixel channel in the color spot region, to obtain a pixel value L' of an aged L pixel channel, where $L'=L+K1\times C1\times L$, L is a pixel value of the L pixel channel before the aging processing, and C1 is a constant. The electronic device performs aging processing on the a pixel channel in the color spot region, to obtain a pixel value a' of an aged a pixel channel, where $a'=a+K2\times C2\times a$, a is a pixel value of the a pixel channel before the aging processing, and C2 is a constant. The electronic device performs aging processing on the b pixel channel in the color spot region, to obtain a pixel value b' of an aged b pixel channel, where $b'=b+K3\times C3\times b$, b is a pixel value of the b pixel channel before the aging processing, and C3 is a constant.

It can be learned that pixel values of the L pixel channel, the a pixel channel, and the b pixel channel in the color spot region are all increased after the aging processing, so that a color of the color spot region after the aging processing becomes yellower, thereby implementing a visual effect of color spot aging.

For example, that the electronic device performs de-aging processing on the color spot region in the face image to obtain the second facial simulated image specifically includes: The electronic device obtains a change coefficient K1 of an L pixel channel, a change coefficient K2 of an a pixel channel, and a change coefficient K3 of a b pixel channel in the color spot region. The electronic device performs de-aging processing on the L pixel channel in the color spot region, to obtain a pixel value L' of a de-aged L pixel channel, where L'=L−K1×C1×L, L is a pixel value of the L pixel channel before the de-aging processing, and C1 is a constant. The electronic device performs de-aging processing on the a pixel channel in the color spot region, to obtain a pixel value a' of a de-aged a pixel channel, where a'=a−K2×C2× a, a is a pixel value of the a pixel channel before the de-aging processing, and C2 is a constant. The electronic device performs de-aging processing on the b pixel channel in the color spot region, to obtain a pixel value b' of a de-aged b pixel channel, where b'=b−K3×C3×b, b is a pixel value of the b pixel channel before the de-aging processing, and C3 is a constant.

It can be learned that pixel values of the L pixel channel, the a pixel channel, and the b pixel channel of the color spot region are all reduced after the aging processing, so that a color of the color spot region after the aging processing becomes lighter, thereby implementing a visual effect of color spot de-aging.

In a possible design method, the skin problem may specifically include a fine line problem. In this case, that the electronic device detects a skin problem that appears in the face image includes: The electronic device detects, in the face image, a fine line region in which the fine line problem appears.

In a possible design method, before the electronic device displays the second interface in response to the first operation of the user in the first interface, the method further includes: The electronic device performs aging processing on the fine line region in the face image to obtain the first facial simulated image. Alternatively, before the electronic device displays the third interface in response to the second operation of the user in the first interface, the method further includes: The electronic device performs de-aging processing on the fine line region in the face image to obtain the second facial simulated image.

For example, that the electronic device performs aging processing on the fine line region in the face image to obtain the first facial simulated image specifically includes: The electronic device obtains a change coefficient D of the fine line region. The electronic device performs de-aging processing on an R pixel channel in the fine line region, to obtain a pixel value R of a de-aged R pixel channel, where R'=R−C5×D, R is a pixel value of the R pixel channel before the de-aging processing, and C5 is a constant. The electronic device performs de-aging processing on a G pixel channel in the fine line region, to obtain a pixel value G of a de-aged G pixel channel, where G'=G−C6×D, G is a pixel value of the G pixel channel before the de-aging processing, and C6 is a constant. The electronic device performs de-aging processing on a B pixel channel in the fine line region, to obtain a pixel value B' of a de-aged B pixel channel, where B'=B−C7×D, R is a pixel value of the B pixel channel before the de-aging processing, and C7 is a constant.

It can be learned that pixel values of the R pixel channel, the G pixel channel, and the B pixel channel of the fine line region are all reduced after the aging processing, so that a color of the fine line region after the aging processing deepens and darkens, thereby implementing a visual effect of fine line aging.

For example, that the electronic device performs de-aging processing on the fine line region in the face image to obtain the second facial simulated image specifically includes: The electronic device obtains a change coefficient D of the fine line region in the face image. The electronic device performs de-aging processing on an R pixel channel in the fine line region, to obtain a pixel value R' of a de-aged R pixel channel, where R'=R+C5×D, R is a pixel value of the R pixel channel before the de-aging processing, and C5 is a constant. The electronic device performs de-aging processing on a G pixel channel in the fine line region, to obtain a pixel value G' of a de-aged G pixel channel, where G'=G+C6×D, G is a pixel value of the G pixel channel before the de-aging processing, and C6 is a constant. The electronic device performs de-aging processing on a B pixel channel in the fine line region, to obtain a pixel value B' of a de-aged B pixel channel, where B'=B+C7×D, R is a pixel value of the B pixel channel before the de-aging processing, and C7 is a constant.

It can be learned that pixel values of the R pixel channel, the G pixel channel, and the B pixel channel of the fine line region are all increased after the de-aging processing, so that a color of the fine line region after the de-aging processing becomes lightened and brightened, thereby implementing a visual effect of fine line aging.

In a possible design method, the first interface may further include an aging progress bar and a slider. In this case, the first operation is a sliding operation of dragging the slider on the aging progress bar by the user, and the method may further include: If it is detected that the slider is dragged to a first position of the aging progress bar, the electronic device displays, in the second interface, a first facial simulated image corresponding to the first position; or if it is detected that the slider is dragged to a second position of the aging progress bar, the electronic device displays, in the second interface, a first facial simulated image corresponding to the second position.

In a possible design method, the first interface may further include a de-aging progress bar and a slider. In this case, the second operation is a sliding operation of dragging the slider on the de-aging progress bar by the user, and the method may further include: If it is detected that the slider is dragged to a first position of the de-aging progress bar, the electronic device displays, in the third interface, a second facial simulated image corresponding to the first position; or if it is detected that the slider is dragged to a second position of the de-aging progress bar, the electronic device displays, in the third interface, a second facial simulated image corresponding to the second position.

In other words, the electronic device may further display, to the user, face images in different degrees of aging/de-aging of the skin problem. For example, the electronic device may display, to the user, aging statuses of the skin problem after different periods of time, so that the user can dynamically sense aging/de-aging statuses of the skin problem in the current face over time.

In a possible design method, the first interface further includes a scoring status or a skin care suggestion for a skin problem in the face image; or the second interface further includes a scoring status or a skin care suggestion for a skin problem in the first facial simulated image; or the third interface further includes a scoring status or a skin care suggestion for a skin problem in the second facial simulated image, so as to intuitively remind the user to pay attention to the skin problem appearing on the face and perform timely repair.

According to a second aspect, this application provides an electronic device, including a touchscreen, one or more processors, one or more memories, and one or more computer programs, where the processor is coupled to both the touchscreen and the memory, the one or more computer programs are stored in the memory, and when the electronic device runs, the processor executes the one or more computer programs stored in the memory, so that the electronic device performs the skin detection method according to any one of the foregoing possible design methods.

According to a third aspect, this application provides a computer storage medium, including computer instructions, where when the computer instructions are run on an electronic device, the electronic device is enabled to perform the skin detection method according to any one of the possible design methods of the first aspect.

According to a fourth aspect, this application provides a computer program product, where when the computer program product is run on an electronic device, the electronic device is enabled to perform the skin detection method according to any one of the possible design methods of the first aspect.

It may be understood that the electronic device described in the second aspect, the computer storage medium described in the third aspect, and the computer program product described in the fourth aspect provided above are all configured to perform the corresponding method provided above. Therefore, for beneficial effects that can be achieved by the electronic device, the computer storage medium, and the computer program product, refer to the beneficial effects of the corresponding method provided above. Details are not described herein again.

DESCRIPTION OF EMBODIMENTS

The following describes implementations of the embodiments in detail with reference to the accompanying drawings.

For example, a skin detection method provided in the embodiments of this application may be applied to an electronic device such as a mobile phone, a tablet computer, a desktop computer, a laptop computer, a notebook computer, an ultra-mobile personal computer (ultra-mobile personal computer, UMPC), a handheld computer, a netbook, a personal digital assistant (personal digital assistant, PDA), a wearable electronic device, or a virtual reality device. This is not limited in the embodiments of this application.

Figure 1:
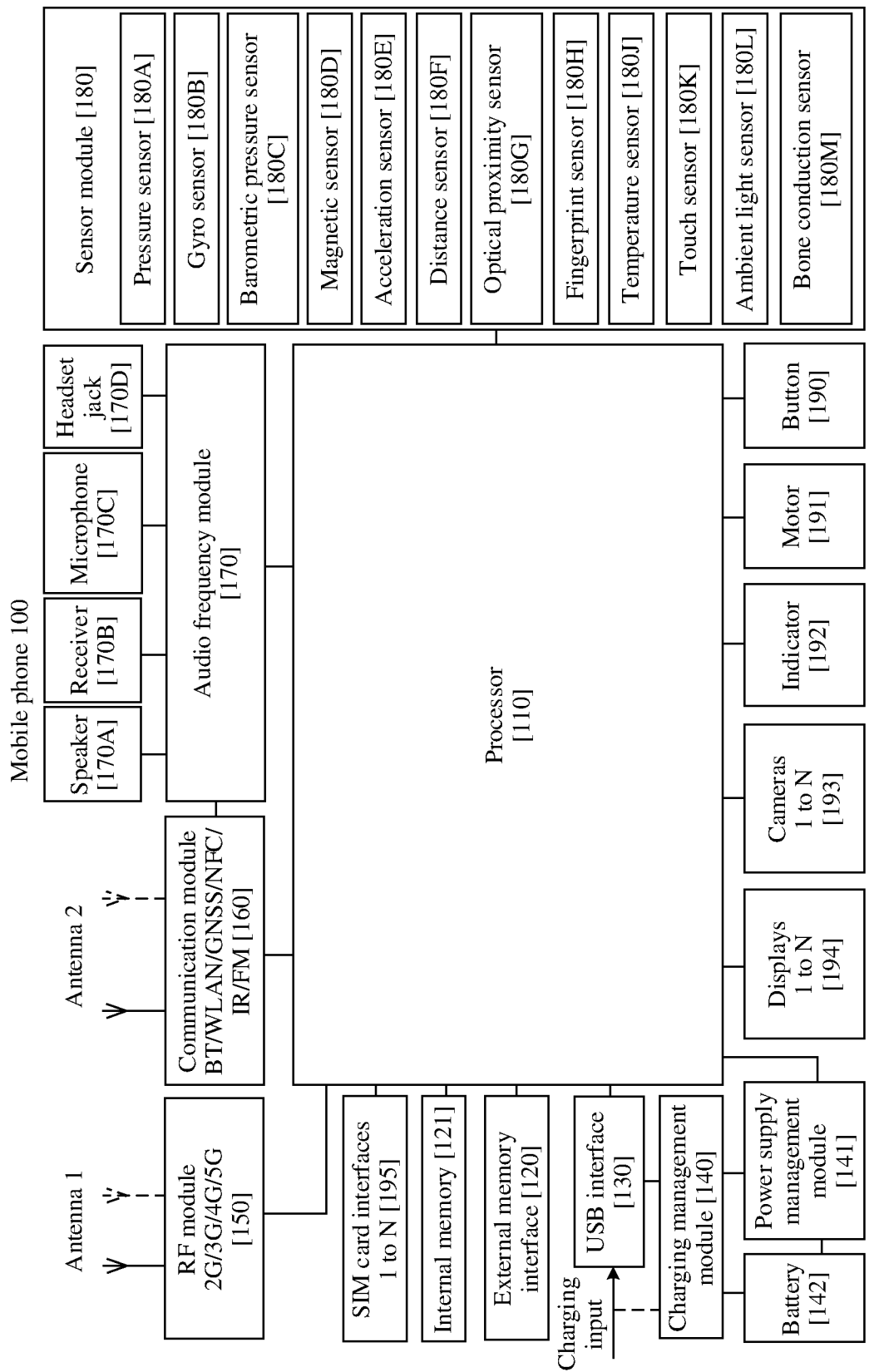
FIG. 1 is a schematic structural diagram 1 of an electronic device according to an embodiment of this application.

For example, a mobile phone 100 is the foregoing electronic device. FIG. 1 is a schematic structural diagram of the mobile phone 100.

The mobile phone 100 may include a processor 110, an external memory interface 120, an internal memory 121, a universal serial bus (universal serial bus, USB) interface 130, a charging management module 140, a power management module 141, a battery 142, an antenna 1, an antenna 2, a mobile communications module 150, a wireless communications module 160, an audio module 170, a speaker 170A, a receiver 170B, a microphone 170C, a headset jack 170D, a sensor module 180, a button 190, a motor 191, an indicator 192, a camera 193, a display 194, a subscriber identification module (subscriber identification module, SIM) card interface 195, and the like. The sensor module 180 may include a pressure sensor 180A, a gyro sensor 180B, a barometric pressure sensor 180C, a magnetic sensor 180D, an acceleration sensor 180E, a distance sensor 180F, an optical proximity sensor 180G, a fingerprint sensor 180H, a temperature sensor 180J, a touch sensor 180K, an ambient light sensor 180L, a bone conduction sensor 180M, and the like.

It may be understood that a structure shown in this embodiment of this application does not constitute a specific limitation on the mobile phone 100. In some other embodiments of this application, the mobile phone 100 may include more or fewer components than those shown in the figure, combine some components, split some components, or have different component arrangements. The components shown in the figure may be implemented by hardware, software, or a combination of software and hardware.

The processor 110 may include one or more processing units. For example, the processor 110 may include an application processor (application processor, AP), a modem processor, a graphics processing unit (graphics processing unit, GPU), an image signal processor (image signal processor, ISP), a controller, a memory, a video codec, a digital signal processor (digital signal processor, DSP), a baseband processor, a neural network processing unit (neural-network processing unit, NPU), and/or the like. Different processing units may be independent devices, or may be integrated into one or more processors.

The controller may be a nerve center and a command center of the mobile phone 100. The controller may generate an operation control signal based on instruction operation code and a time sequence signal, to complete control of instruction reading and instruction execution.

The memory may be further disposed in the processor 110, and is configured to store an instruction and data. In some embodiments, the memory in the processor 110 is a cache memory. The memory may store an instruction or data just used or cyclically used by the processor 110. If the processor 110 needs to use the instruction or the data again, the processor 110 may directly invoke the instruction or the data from the memory. This avoids repeated access and reduces a waiting time of the processor 110, thereby improving system efficiency.

In some embodiments, the processor 110 may include one or more interfaces. The interface may include an inter-integrated circuit (inter-integrated circuit, I2C) interface, an inter-integrated circuit sound (inter-integrated circuit sound, I2S) interface, a pulse code modulation (pulse code modulation, PCM) interface, a universal asynchronous receiver/transmitter (universal asynchronous receiver/transmitter, UART) interface, a mobile industry processor interface (mobile industry processor interface, MIPI), a general-purpose input/output (general-purpose input/output, GPIO) interface, a subscriber identification module (subscriber identity module, SIM) interface, a universal serial bus (universal serial bus, USB) interface, and/or the like.

The I2C interface is a two-way synchronization serial bus, and includes a serial data line (serial data line, SDA) and a serial clock line (serial clock line, SCL). In some embodiments, the processor 110 may include a plurality of groups of I2C buses. The processor 110 may be separately coupled to the touch sensor 180K, a charger, a flash, the camera 193, and the like through different I2C bus interfaces. For example, the processor 110 may be coupled to the touch sensor 180K through the I2C interface, so that the processor 110 communicates with the touch sensor 180K through the I2C bus interface, to implement a touch function of the mobile phone 100.

The I2S interface may be configured to perform audio communication. In some embodiments, the processor 110 may include a plurality of groups of I2S buses. The processor 110 may be coupled to the audio module 170 through the I2S bus, to implement communication between the processor 110 and the audio module 170. In some embodiments, the audio module 170 may transmit an audio signal to the wireless communications module 160 through the I2S interface, to implement a function of answering a call by using a Bluetooth headset.

The PCM interface may also be configured to: perform audio communication, and sample, quantize, and code an analog signal. In some embodiments, the audio module 170 may be coupled to the wireless communications module 160 through a PCM bus interface. In some embodiments, the audio module 170 may alternatively transmit the audio signal to the wireless communications module 160 through the PCM interface, to implement a function of answering a call by using a Bluetooth headset. Both the I2S interface and the PCM interface may be configured to perform audio communication.

The UART interface is a universal serial data bus, and is configured to perform asynchronous communication. The bus may be a two-way communications bus, and converts to-be-transmitted data between serial communication and parallel communication. In some embodiments, the UART interface is usually configured to connect the processor 110 to the wireless communications module 160. For example, the processor 110 communicates with a Bluetooth module in the wireless communications module 160 through the UART interface, to implement a Bluetooth function. In some embodiments, the audio module 170 may transmit an audio signal to the wireless communications module 160 through the UART interface, to implement a function of playing music by using the Bluetooth headset.

The MIPI interface may be configured to connect the processor 110 to a peripheral component such as the display 194 or the camera 193. The MIPI interface includes a camera serial interface (camera serial interface, CSI), a display serial interface (display serial interface, DSI), and the like. In some embodiments, the processor 110 communicates with the camera 193 through the CSI interface, to implement a photographing function of the mobile phone 100. The processor 110 communicates with the display 194 through the DSI interface, to implement a display function of the mobile phone 100.

The GPIO interface may be configured through software. The GPIO interface may be configured as a control signal or a data signal. In some embodiments, the GPIO interface may be configured to connect the processor 110 to the camera 193, the display 194, the wireless communications module 160, the audio module 170, the sensor module 180, and the like. The GPIO interface may alternatively be configured as the I2C interface, the I2S interface, the UART interface, the MIPI interface, or the like.

The USB interface 130 is an interface that conforms to a USB standard specification, and may be specifically a mini USB interface, a micro USB interface, a USB Type-C interface, or the like. The USB interface 130 may be configured to connect to a charger to charge the mobile phone 100, or may be configured to transmit data between the mobile phone 100 and a peripheral device, or may be configured to connect to a headset to play audio by using the headset. Alternatively, the interface may be configured to connect to another electronic device such as an AR device.

It may be understood that an interface connection relationship between the modules illustrated in the embodiments of this application is merely an example for description, and does not constitute a limitation on a structure of the mobile phone 100. In some other embodiments of this application, the mobile phone 100 may alternatively use an interface connection manner different from that in the foregoing embodiments, or use a combination of a plurality of interface connection manners.

The charging management module 140 is configured to receive charging input from the charger. The charger may be a wireless charger or a wired charger. In some embodiments of wired charging, the charging management module 140 may receive charging input from the wired charger through the USB interface 130. In some embodiments of wireless charging, the charging management module 140 may receive wireless charging input by using a wireless charging coil of the mobile phone 100. The charging management module 140 supplies power to the electronic device by using the power management module 141 while charging the battery 142.

The power management module 141 is configured to connect the battery 142 and the charging management module 140 to the processor 110. The power management module 141 receives input from the battery 142 and/or the charging management module 140, and supplies power to the processor 110, the internal memory 121, an external memory, the display 194, the camera 193, the wireless communications module 160, and the like. The power management module 141 may be further configured to monitor parameters such as a battery capacity, a quantity of battery cycles, and a battery health status (electric leakage or impedance). In some other embodiments, the power management module 141 may alternatively be disposed in the processor 110. In some other embodiments, the power management module 141 and the charging management module 140 may alternatively be disposed in a same device.

A wireless communication function of the mobile phone 100 may be implemented by using the antenna 1, the antenna 2, the mobile communications module 150, the wireless communications module 160, the modem processor, the baseband processor, and the like.

The antenna 1 and the antenna 2 are configured to: transmit and receive electromagnetic wave signals. Each antenna in the mobile phone 100 may be configured to cover one or more communication bands. Different antennas may be further multiplexed to improve antenna utilization. For example, the antenna 1 may be multiplexed as a diversity antenna in a wireless local area network. In some other embodiments, an antenna may be used in combination with a tuning switch.

The mobile communications module 150 may provide a wireless communication solution that includes 2G/3G/4G/5G or the like and that is applied to the mobile phone 100. The mobile communications module 150 may include at least one filter, a switch, a power amplifier, a low noise amplifier (low noise amplifier, LNA), and the like. The mobile communications module 150 may receive an electromagnetic wave through the antenna 1, perform processing such as filtering or amplification on the received electromagnetic wave, and transmit a processed electromagnetic wave to the modem processor for demodulation. The mobile communications module 150 may further amplify a signal modulated by the modem processor, and convert the signal into an electromagnetic wave for radiation through the antenna 1. In some embodiments, at least some function modules of the mobile communications module 150 may be disposed in the processor 110. In some embodiments, at least some function modules of the mobile communications module 150 and at least some modules of the processor 110 may be disposed in a same device.

The modem processor may include a modulator and a demodulator. The modulator is configured to modulate a to-be-sent low-frequency baseband signal into a medium or high-frequency signal. The demodulator is configured to demodulate a received electromagnetic wave signal into a low-frequency baseband signal. Then, the demodulator transmits the low-frequency baseband signal obtained through demodulation to the baseband processor for processing. The low-frequency baseband signal is processed by the baseband processor, and then transmitted to the application processor. The application processor outputs a sound signal through an audio device (which is not limited to the speaker 170A, the receiver 170B, or the like), or displays an image or a video through the display 194. In some embodiments, the modem processor may be an independent component. In some other embodiments, the modem processor may be independent of the processor 110, and is disposed in a same device as the mobile communications module 150 or another function module.

The wireless communications module 160 may provide a wireless communication solution that includes a wireless local area network (wireless local area networks, WLAN) (for example, a wireless fidelity (wireless fidelity, Wi-Fi) network), Bluetooth (Bluetooth, BT), a global navigation satellite system (global navigation satellite system, GNSS), frequency modulation (frequency modulation, FM), a near field communication (near field communication, NFC) technology, an infrared (infrared, IR) technology, or the like and that is applied to the mobile phone 100. The wireless communications module 160 may be one or more components integrated into at least one communications processing module. The wireless communications module 160 receives an electromagnetic wave through the antenna 2, performs frequency modulation and filtering processing on an electromagnetic wave signal, and sends a processed signal to the processor 110. The wireless communications module 160 may further receive a to-be-sent signal from the processor 110, perform frequency modulation and amplification on the signal, and convert the signal into an electromagnetic wave for radiation through the antenna 2.

In some embodiments, the antenna 1 and the mobile communications module 150 of the mobile phone 100 are coupled, and the antenna 2 and the wireless communications module 160 of the mobile phone 100 are coupled, so that the mobile phone 100 can communicate with a network and another device by using a wireless communications technology. The wireless communications technology may include a global system for mobile communications (global system for mobile communications, GSM), a general packet radio service (general packet radio service, GPRS), code division multiple access (code division multiple access, CDMA), wideband code division multiple access (wideband code division multiple access, WCDMA), time-division code division multiple access (time-division code division multiple access, TD-SCDMA), long term evolution (long term evolution, LTE), BT, a GNSS, a WLAN, NFC, FM, an IR technology, and/or the like. The GNSS may include a global positioning system (global positioning system, GPS), a global navigation satellite system (global navigation satellite system, GLONASS), a BeiDou navigation satellite system (Beidou navigation satellite system, BDS), a quasi-zenith satellite system (quasi-zenith satellite system, QZSS), and/or a satellite based augmentation system (satellite based augmentation systems, SBAS).

The mobile phone 100 implements a display function by using the GPU, the display 194, the application processor, and the like. The GPU is a microprocessor for image processing, and connects the display 194 to the application processor. The GPU is configured to: perform mathematical and geometric calculation, and render an image. The processor 110 may include one or more GPUs that execute a program instruction to generate or change display information.

The display 194 is configured to display an image, a video, and the like. The display 194 includes a display panel. The display panel may be a liquid crystal display (liquid crystal display, LCD), an organic light-emitting diode (organic light-emitting diode, OLED), an active-matrix organic light emitting diode (active-matrix organic light emitting diode, AMOLED), a flexible light-emitting diode (flex light-emitting diode, FLED), a mini LED, a micro LED, a micro OLED, quantum dot light emitting diodes (quantum dot light emitting diodes, QLED), or the like. In some embodiments, the mobile phone 100 may include one or N displays 194, where N is a positive integer greater than 1.

The mobile phone 100 may implement a photographing function by using the ISP, the camera 193, the video codec, the GPU, the display 194, the application processor, and the like.

The ISP is configured to process data fed back by the camera 193. For example, during photographing, a shutter is pressed, and light is transmitted to a photosensitive element of the camera through a lens. An optical signal is converted into an electrical signal, and the photosensitive element of the camera transmits the electrical signal to the ISP for processing, to convert the electrical signal into a visible image. The ISP may further perform algorithm optimization on noise, brightness, and complexion of the image. The ISP may further optimize parameters such as exposure and color temperature of a photographing scenario. In some embodiments, the ISP may be disposed in the camera 193.

Figure 2:
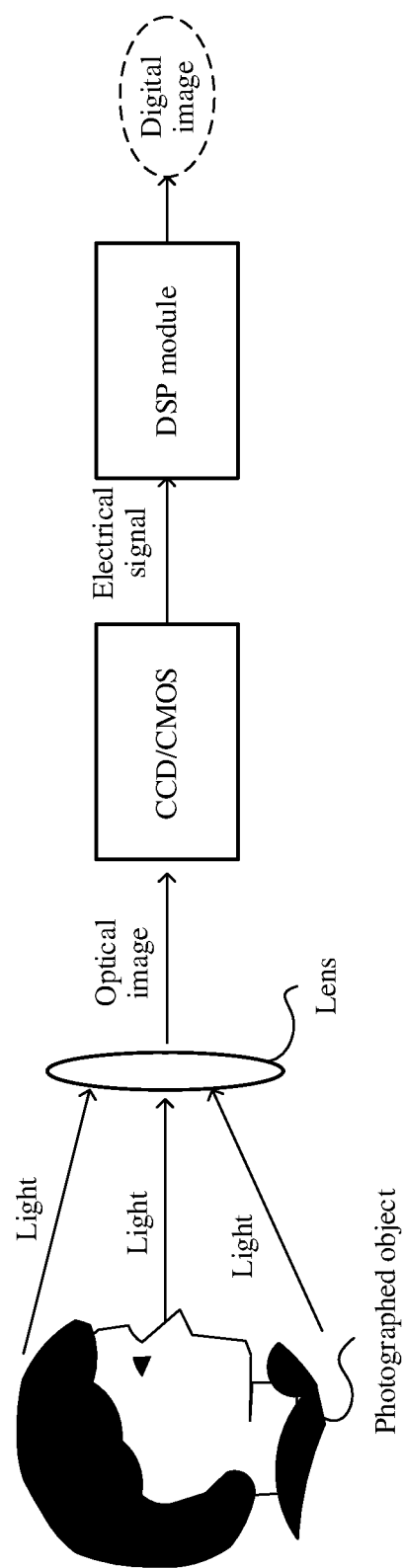
FIG. 2 is a schematic diagram of a photographing principle according to an embodiment of this application.

The camera 193 is configured to capture a static image or a video. In some embodiments, the mobile phone 100 may include one or N cameras 193, where N is a positive integer greater than 1. The camera 193 may be a front-facing camera or a rear-facing camera. As shown in FIG. 2, the camera 193 usually includes a lens (lens) and a photosensitive element (for example, a sensor). The photosensitive element may be any photosensitive element such as a CCD (charge-coupled device, charge-coupled device) or a CMOS (complementary metal oxide semiconductor, complementary metal oxide semiconductor).

Still as shown in FIG. 2, in a photographing process, reflected light of a to-be-photographed object passes through the lens, and then an optical image may be generated. The optical image is projected onto the photosensitive element. The photosensitive element converts a received optical signal into an electrical signal. Further, the camera 193 sends the obtained electrical signal to a DSP (Digital Signal Processing, digital signal processing) module for digital signal processing. Finally, a digital image is obtained. The digital image may be output on the mobile phone 100 through the display 194, or the digital image may be stored in the internal memory 121.

Figure 3C:
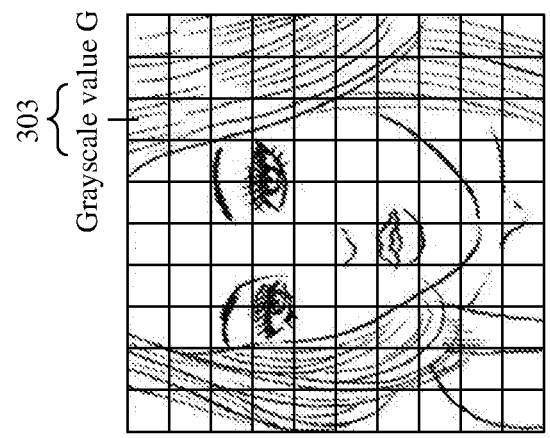
FIG. 3(a), FIG. 3(b), and FIG. 3(c) are a schematic diagram of a color space conversion principle according to an embodiment of this application.
Figure 3B:
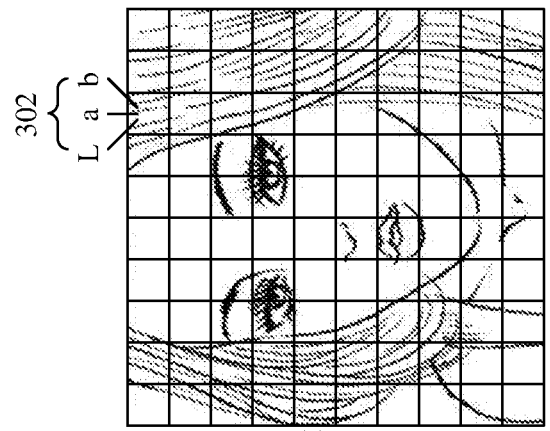
Figure 3A:
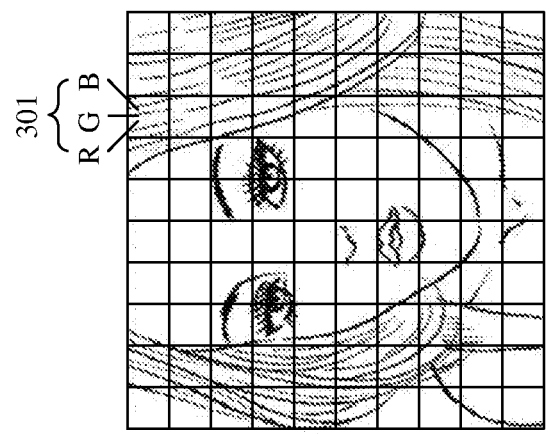

Usually, the DSP may encode, by using an RGB encoding mode, an electrical signal output by the photosensitive element, to obtain a digital image (which may be referred to as an RGB format image in subsequent embodiments) in an RGB color space. In the RGB encoding mode, various colors are obtained by changing three pixel channels, namely, red (R), green (G), and blue (B), and superimposing the three pixel channels. RGB respectively represent colors of the three pixel channels: red, green, and blue. As shown in FIG. 3(*a*), an RGB format image 1 includes 10×10 pixel units 301, each pixel unit 301 includes three pixel channels R, G, and B, and each pixel channel has a corresponding pixel value. For example, a value range of each pixel channel is [0, 255], a larger value indicates a lighter color, and a smaller value indicates a darker color.

For example, the mobile phone 100 may convert an RGB format image into a digital image (which may be referred to as a Lab format image in subsequent embodiments) in a Lab color space. An L component in the Lab color space is used to represent lightness of a pixel unit, and has a value range of [0, 100], which represents from pure black to pure white; a represents a range from red to green, and has a value range of [127, −128]; b represents a range from yellow to blue, and has a value range of [127, −128]. As shown in FIG. 3(*b*), after the mobile phone 100 converts the RGB format image 1 into a Lab format image 2, the image 2 still includes 10×10 pixel units 302. A difference is that each pixel unit 302 includes three pixel channels L, a, and b, and each pixel channel has a corresponding pixel value. After the three pixel channels L, a, and b are superposed, a pixel unit 302 is formed. When a value obtained after the three pixel channels L, a, and b are superposed is larger, a color of the pixel unit 302 is yellower.

In addition, the mobile phone 100 may convert an RGB format image into a digital image (which may be referred to as a gray format image in subsequent embodiments) in a grayscale color space. As shown in FIG. 3(*c*), the mobile phone 100 may calculate a grayscale value G of each pixel unit 303 according to a grayscale formula, to obtain a corresponding grayscale format image 3. For example, the grayscale formula is: G=R×0.299+G×0.587+B×0.114.

The video codec is configured to: compress or decompress a digital video. The mobile phone 100 may support one or more video codecs. In this way, the mobile phone 100 can play or record videos in a plurality of coding formats, for example, moving picture experts group (moving picture experts group, MPEG)-1, MPEG-2, MPEG-3, and MPEG-4.

The NPU is a neural-network (neural-network, NN) computing processor, quickly processes input information by referring to a structure of a biological neural network, for example, by referring to a transfer mode between human brain neurons, and may further continuously perform self-learning. Applications such as intelligent cognition of the mobile phone 100, such as image recognition, facial recognition, speech recognition, and text understanding, can be implemented by using the NPU.

The external memory interface 120 may be configured to connect to an external storage card such as a micro SD card, to extend a storage capability of the mobile phone 100. The external storage card communicates with the processor 110 through the external memory interface 120, to implement a data storage function. For example, files such as music and a video are stored in the external storage card.

The internal memory 121 may be configured to store computer executable program code. The executable program code includes an instruction. The processor 110 runs the instruction stored in the internal memory 121, to implement various function applications of the mobile phone 100 and data processing. The internal memory 121 may include a program storage area and a data storage area. The program storage area may store an operating system, an application required by at least one function (for example, a sound playing function or an image playing function), and the like. The data storage area may store data (for example, audio data or an address book) created during use of the mobile phone 100, and the like. In addition, the internal memory 121 may include a high-speed random access memory, and may further include a nonvolatile memory, for example, at least one magnetic disk storage device, a flash memory device, or a universal flash storage (universal flash storage, UFS).

The mobile phone 100 may implement an audio function such as music playing or recording by using the audio module 170, the speaker 170A, the receiver 170B, the microphone 170C, the headset jack 170D, the application processor, and the like.

The audio module 170 is configured to convert digital audio information into an analog audio signal for output, and is also configured to convert analog audio input into a digital audio signal. The audio module 170 may be further configured to: code and decode an audio signal. In some embodiments, the audio module 170 may be disposed in the processor 110, or some function modules of the audio module 170 are disposed in the processor 110.

The speaker 170A, also referred to as a "horn", is configured to convert an audio electrical signal into a sound signal. The mobile phone 100 may listen to music by using the speaker 170A, or listen to a hands-free call.

The receiver 170B, also referred to as an "earpiece", is configured to convert an audio electrical signal into a sound signal. When a call is answered or voice information is received by using the mobile phone 100, the receiver 170B may be put close to a human ear to listen to a voice.

The microphone 170C, also referred to as a "mike" or a "microphone", is configured to convert a sound signal into an electrical signal. When making a call or sending voice information, a user may make a sound by moving a human mouth close to the microphone 170C to input a sound signal to the microphone 170C. At least one microphone 170C may be disposed in the mobile phone 100. In some other embodiments, two microphones 170C may be disposed in the mobile phone 100, to collect a sound signal and further implement a noise reduction function. In some other embodiments, three, four, or more microphones 170C may alternatively be disposed in the mobile phone 100, to collect a sound signal, reduce noise, further identify a sound source, implement a directional recording function, and the like.

The headset jack 170D is configured to connect to a wired headset. The headset jack 170D may be the USB interface 130 or a 3.5 mm open mobile terminal platform (open mobile terminal platform, OMTP) standard interface or cellular telecommunications industry association of the USA (cellular telecommunications industry association of the USA, CTIA) standard interface.

The pressure sensor 180A is configured to sense a pressure signal, and can convert the pressure signal into an electrical signal. In some embodiments, the pressure sensor 180A may be disposed on the display 194. There are a plurality of types of pressure sensors 180A, for example, a resistive pressure sensor, an inductive pressure sensor, a capacitive pressure sensor. The capacitive pressure sensor may include at least two parallel plates made of conductive materials. When a force is applied to the pressure sensor 180A, capacitance between electrodes changes. The mobile phone 100 determines pressure intensity based on the change of the capacitance. When a touch operation is performed on the display 194, the mobile phone 100 detects intensity of the touch operation by using the pressure sensor 180A. The mobile phone 100 may also calculate a touch location based on a detection signal of the pressure sensor 180A. In some embodiments, touch operations that are performed at a same touch location but have different touch operation intensity may correspond to different operation instructions. For example, when a touch operation whose touch operation intensity is less than a first pressure threshold is performed on a Messages icon, an instruction for viewing an SMS message is executed. When a touch operation whose touch operation intensity is greater than or equal to the first pressure threshold is performed on a Messages icon, an instruction for creating a new SMS message is executed.

The gyro sensor 180B may be configured to determine a moving posture of the mobile phone 100. In some embodiments, an angular velocity of the mobile phone 100 around three axes (namely, x, y, and z axes) may be determined by using the gyro sensor 180B. The gyro sensor 180B may be configured to perform image stabilization during photographing. For example, when a shutter is pressed, the gyro sensor 180B detects an angle at which the mobile phone 100 jitters, obtains, through calculation based on the angle, a distance for which a lens module needs to compensate, and allows a lens to cancel the jitter of the mobile phone 100 through reverse motion, to implement image stabilization. The gyro sensor 180B may be further used in navigation and motion sensing game scenarios.

The barometric pressure sensor 180C is configured to measure barometric pressure. In some embodiments, the mobile phone 100 calculates an altitude by using the barometric pressure measured by the barometric pressure sensor 180C, to assist in positioning and navigation.

The magnetic sensor 180D includes a Hall sensor. The mobile phone 100 may detect opening and closing of a flip leather case by using the magnetic sensor 180D. In some embodiments, when the mobile phone 100 is a clamshell phone, the mobile phone 100 may detect opening/closing of a flip cover based on the magnetic sensor 180D. Further, a feature such as automatic unlocking of the flip cover is set based on a detected opening/closing state of the leather case or a detected opening/closing state of the flip cover.

The acceleration sensor 180E may detect values of acceleration in various directions (usually on three axes) of the mobile phone 100. When the mobile phone 100 is still, a value and a direction of gravity may be detected. The acceleration sensor 180E may be further configured to identify a posture of the electronic device, and is applied to an application such as switching between landscape mode and portrait mode or a pedometer.

The distance sensor 180F is configured to measure a distance. The mobile phone 100 may measure a distance through infrared light or a laser. In some embodiments, in a photographing scenario, the mobile phone 100 may measure a distance by using the distance sensor 180F, to implement fast focusing.

For example, the optical proximity sensor 180G may include a light-emitting diode (LED) and an optical detector, for example, a photodiode. The light-emitting diode may be an infrared light-emitting diode. The mobile phone 100 emits infrared light by using the light-emitting diode. The mobile phone 100 detects infrared reflected light from a nearby object by using the photodiode. When sufficient reflected light is detected, the mobile phone 100 may determine that there is an object near the mobile phone 100. When insufficient reflected light is detected, the mobile phone 100 may determine that there is no object near the mobile phone 100. The mobile phone 100 may detect, by using the optical proximity sensor 180G, that the user holds the mobile phone 100 close to an ear to make a call, so as to automatically turn off a screen for power saving. The optical proximity sensor 180G may also be used in a leather case mode or a pocket mode to automatically unlock or lock the screen.

The ambient light sensor 180L is configured to sense luminance of ambient light. The mobile phone 100 may adaptively adjust luminance of the display 194 based on the sensed luminance of the ambient light. The ambient light sensor 180L may also be configured to automatically adjust white balance during photographing. The ambient light sensor 180L may also cooperate with the optical proximity sensor 180G to detect whether the mobile phone 100 is in a pocket to prevent an accidental touch.

The fingerprint sensor 180H is configured to collect a fingerprint. The mobile phone 100 may use a feature of the collected fingerprint to implement fingerprint unlocking, application access locking, fingerprint photographing, fingerprint call answering, and the like.

The temperature sensor 180J is configured to detect a temperature. In some embodiments, the mobile phone 100 executes a temperature processing policy based on the temperature detected by the temperature sensor 180J. For example, when the temperature reported by the temperature sensor 180J exceeds a threshold, the mobile phone 100 lowers performance of a processor near the temperature sensor 180J, to reduce power consumption for thermal protection. In some other embodiments, when the temperature is less than another threshold, the mobile phone 100 heats the battery 142 to prevent the mobile phone 100 from being shut down abnormally because of a low temperature. In some other embodiments, when the temperature is less than still another threshold, the mobile phone 100 boosts an output voltage of the battery 142 to avoid abnormal shutdown caused by a low temperature.

The touch sensor 180K is also referred to as a "touch panel". The touch sensor 180K may be disposed on the display 194, and the touch sensor 180K and the display 194 form a touchscreen, which is also referred to as a "touchscreen". The touch sensor 180K is configured to detect a touch operation performed on or near the touch sensor 180K. The touch sensor may transfer the detected touch operation to the application processor, to determine a type of a touch event. Visual output related to the touch operation may be provided by using the display 194. In some other embodiments, the touch sensor 180K may alternatively be disposed on a surface of the mobile phone 100 and is at a location different from that of the display 194.

The bone conduction sensor 180M may obtain a vibration signal. In some embodiments, the bone conduction sensor 180M may obtain a vibration signal of a vibration bone of a human vocal part. The bone conduction sensor 180M may also be in contact with a human pulse, and receive a blood pressure beating signal. In some embodiments, the bone conduction sensor 180M may alternatively be disposed in the headset to form a bone conduction headset. The audio module 170 may obtain a voice signal through parsing based on the vibration signal that is of the vibration bone of the vocal part and that is obtained by the bone conduction sensor 180M, to implement a voice function. The application processor may parse heart rate information based on the blood pressure beating signal obtained by the bone conduction sensor 180M, to implement a heart rate detection function.

The button 190 includes a power button, a volume button, and the like. The button 190 may be a mechanical button, or may be a touch button. The mobile phone 100 receives button input, and generates button signal input related to a user setting and function control of the mobile phone 100.

The motor 191 may generate a vibration prompt. The motor 191 may be configured to produce an incoming call vibration prompt and a touch vibration feedback. For example, touch operations performed on different applications (for example, photographing and audio playing) may correspond to different vibration feedback effects. The motor 191 may also correspond to different vibration feedback effects for touch operations performed on different areas of the display 194. Different application scenarios (for example, a time reminder, information receiving, an alarm clock, and a game) may also correspond to different vibration feedback effects. A touch vibration feedback effect may be further customized.

The indicator 192 may be an indicator light, and may be configured to indicate a charging status and a power change, or may be configured to indicate a message, a missed call, a notification, and the like.

The SIM card interface 195 is configured to connect to a SIM card. The SIM card may be inserted into the SIM card interface 195 or plugged from the SIM card interface 195, to implement contact with or separation from the mobile phone 100. The mobile phone 100 may support one or N SIM card interfaces, where N is a positive integer greater than 1. The SIM card interface 195 may support a nano-SIM card, a micro-SIM card, a SIM card, and the like. A plurality of cards may be simultaneously inserted into a same SIM card interface 195. The plurality of cards may be of a same type or of different types. The SIM card interface 195 may also be compatible with different types of SIM cards. The SIM card interface 195 may also be compatible with an external storage card. The mobile phone 100 interacts with a network by using the SIM card, to implement functions such as calling and data communication. In some embodiments, the mobile phone 100 uses an eSIM, namely, an embedded SIM card. The eSIM card may be embedded in the mobile phone 100, and cannot be separated from the mobile phone 100.

Figure 4:
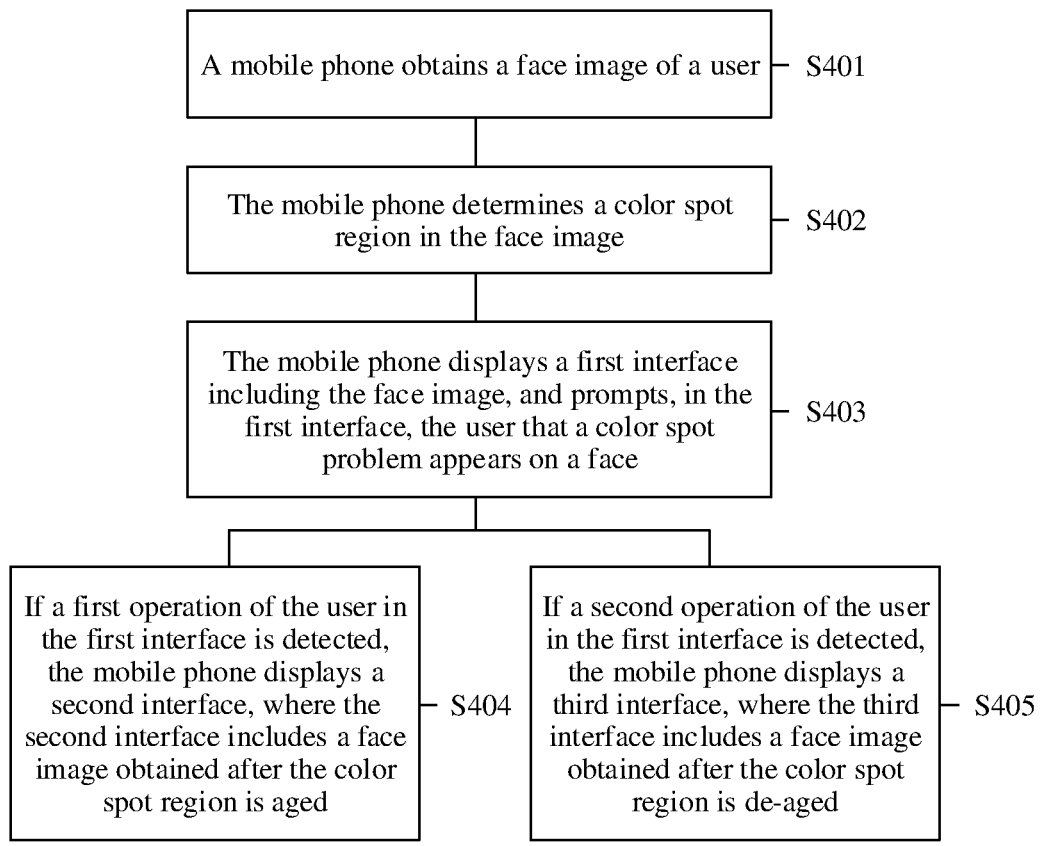
FIG. 4 is a schematic flowchart 1 of a skin detection method according to an embodiment of this application.

The following describes, in detail with reference to the accompanying drawings, a skin detection method provided in an embodiment of this application. As shown in FIG. 4, an example in which a mobile phone is an electronic device is used. The method includes steps S401 to S405.

S401. The mobile phone obtains a face image of a user.

Figure 5:
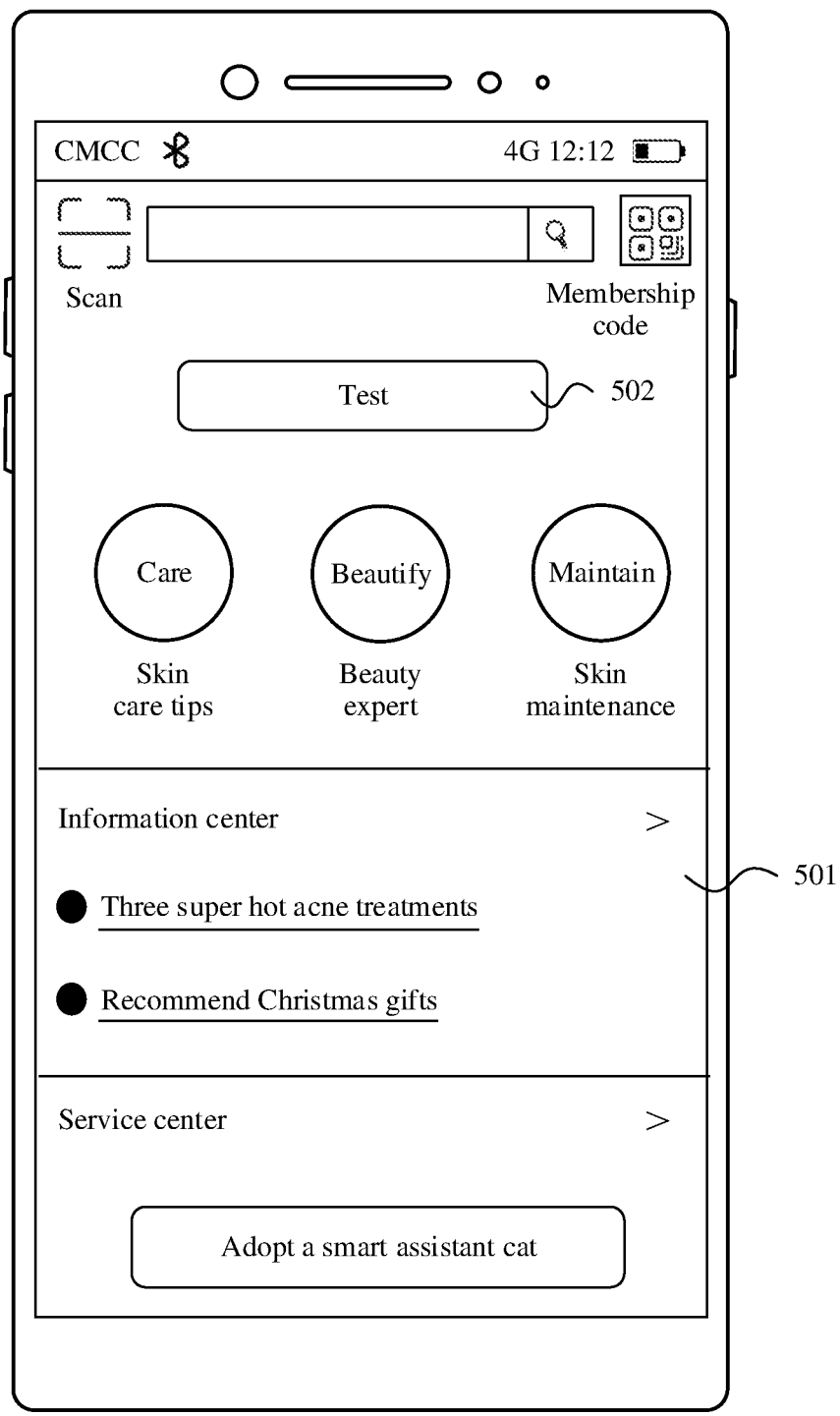
FIG. 5 is a schematic diagram 1 of a scenario of a skin detection method according to an embodiment of this application.

For example, a skin detection app (or an app with a skin detection function) may be installed on the mobile phone. If an operation of starting the skin detection app by a user is detected, as shown in FIG. 5, the mobile phone may start the skin detection app and display an interface 501 of the skin detection app. A test button 502 may be set in the interface 501, and the button 502 may be configured to enable a skin detection function.

Figure 6:
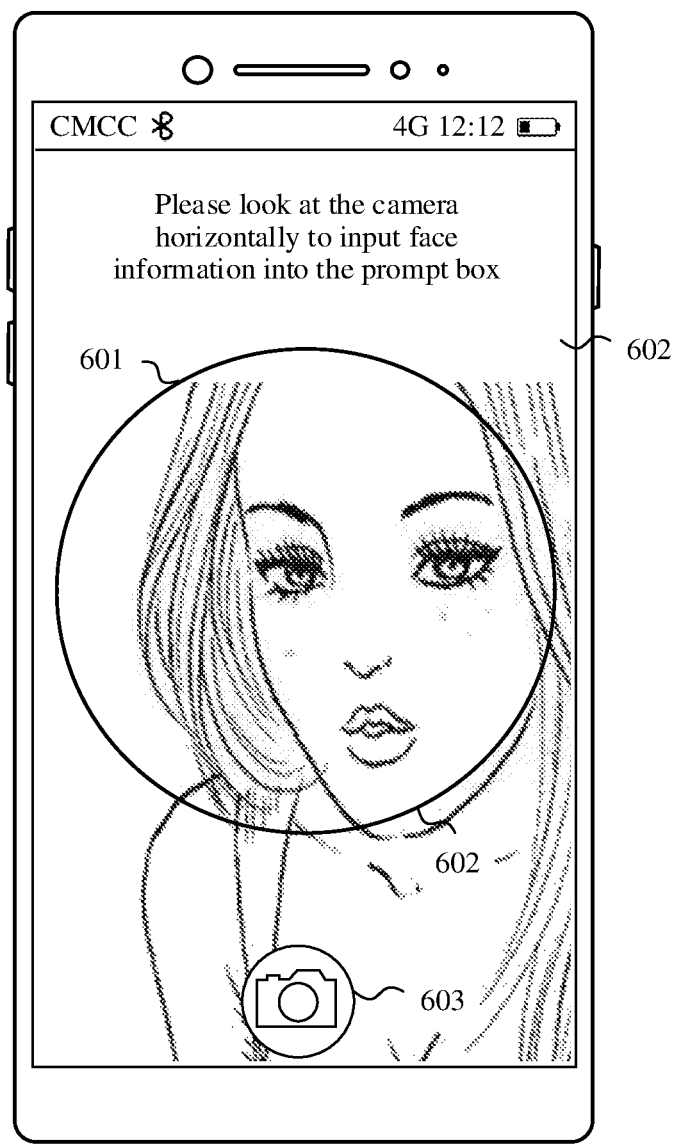
FIG. 6 is a schematic diagram 2 of a scenario of a skin detection method according to an embodiment of this application.

If it is detected that the user taps the button 502, the mobile phone may invoke a camera APP to open a camera to capture a current photographing picture. As shown in FIG. 6, the mobile phone may display the captured photographing picture 601 in a preview interface 602. In addition, the mobile phone may prompt the user to move the mobile phone to input a face into the photographing picture 601. For example, the mobile phone may prompt, by using a text in the preview interface 601, the user to use a front-facing camera to photograph a face image. For another example, the mobile phone may prompt, in a voice form, the user to look at a rear-facing camera horizontally, and adjust a distance between the mobile phone and the user, so that the mobile phone can capture the face image of the user in the photographing picture 601.

When capturing the photographing picture 601, the mobile phone may identify, by using a preset face detection algorithm, whether the photographing picture 601 includes a face that meets a preset size. If it is detected that the photographing picture 601 includes a face that meets the preset size, the mobile phone may automatically perform a photographing operation to obtain an image in the current photographing picture 601, where the image includes a face image of the user. Certainly, the user may alternatively manually tap a photographing button 603 in the preview interface 602. In response to an operation of tapping the photographing button 603 by the user, the mobile phone may save an accordingly obtained photographing picture 601 as a photo in a memory.

In some other embodiments, after detecting that the user enables the skin detection function, the mobile phone may alternatively prompt the user to select a photo including the user's face from an album, so that the mobile phone may extract, by using a face detection algorithm, the face image of the user from the photo selected by the user. Certainly, the face image may alternatively be obtained by the mobile phone from a server or another electronic device. This is not limited in this embodiment of this application.

S402. The mobile phone determines a color spot region in the face image.

After obtaining the face image of the user, the mobile phone may extract, by using a preset color spot detection algorithm, a color spot region in which a color spot exists from the face image. Alternatively, after obtaining the face image of the user, the mobile phone may first prompt the user to select a detection item needing to be detected. For example, the detection item may include a color spot, a wrinkle, acne, a blackhead, or the like. If it is detected that the user selects color spot detection as the detection item, the mobile phone may extract, by using the preset color spot detection algorithm, the color spot region in which the color spot exists from the face image. It may be understood that a person skilled in the art may set the color spot detection algorithm based on actual experience or an actual algorithm. This is not limited in this embodiment of this application.

Figure 7:
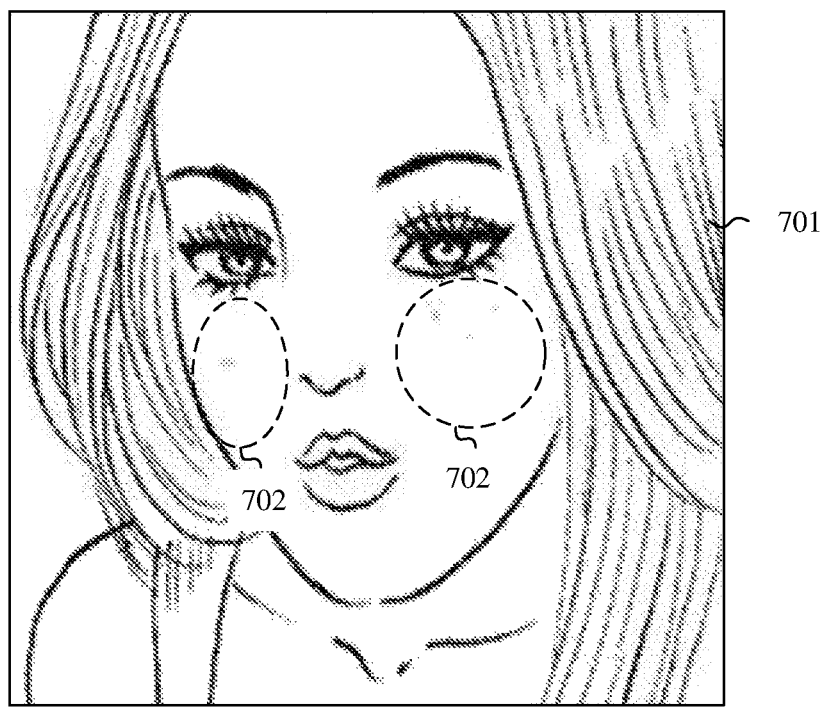
FIG. 7 is a schematic diagram 3 of a scenario of a skin detection method according to an embodiment of this application.

For example, the mobile phone may first extract a region of interest (region of interest, ROI) from the face image. For example, as shown in FIG. 7, the mobile phone may determine a cheek region 702 in the face image 701 as the ROI by extracting a feature point in the face image 701. Further, the mobile phone may determine, based on a pixel value of each pixel unit in the cheek region 702, a candidate pixel unit that may be a color spot in the cheek region 702. The mobile phone may determine the candidate pixel unit in the cheek region 702 in a plurality of manners. The following provides three manners of determining the candidate pixel unit. This is not limited in this embodiment of this application.

Manner 1: The mobile phone may calculate an average value j1 and a variance f1 of pixel values of all pixel units in the cheek region 702. Further, the mobile phone may calculate a first threshold Y1 used for selecting the candidate pixel unit, where Y1=j1−c1×f1, and c1 is a preset constant. The first threshold Y1 may reflect an average level of image color darkness/lightness in the cheek region 702. Further, the mobile phone may compare a pixel value of each pixel unit in the cheek region 702 with a value of the first threshold Y1. If a pixel value of a pixel unit p, is less than the first threshold Y1, which indicates that a color of the pixel unit in the cheek region 702 is relatively dark, the mobile phone may determine the pixel unit p, as the candidate pixel unit of the color spot. In this way, the mobile phone may extract one or more candidate pixel units from the cheek region 702.

Manner 2: The mobile phone may set a detection box whose size is n×n, and a size of the detection box is generally less than a size of the ROI (namely, the cheek region 702). Further, the mobile phone may move the detection box within the cheek region 702 at a specific step. Each time after the detection box is moved, the mobile phone may calculate an average value j2 and a variance f2 of pixel values of all pixel units in a current detection box. Further, the mobile phone may calculate a second threshold Y2 used for selecting a candidate pixel unit, where Y2=j2−c2×f2, and c2 is a preset constant. The second threshold Y2 may reflect an average level of image color darkness/lightness in the current detection box. Further, the mobile phone may compare a pixel value of each pixel unit in the detection box with a value of the second threshold Y2. If a pixel value of a pixel unit pi is less than the second threshold Y2, which indicates that a color of the pixel unit in the current detection box is relatively dark, the mobile phone may determine the pixel unit as the candidate pixel unit of the color spot. By traversing the detection boxes in the cheek region 702, the mobile phone may determine a candidate pixel unit in each detection box, so as to obtain one or more candidate pixel units in the entire cheek region 702.

Manner 3: The mobile phone may use a full set of the candidate pixel unit determined in manner 1 and the candidate pixel unit determined in manner 2 as all candidate pixel units in the cheek region 702.

After the mobile phone determines the plurality of candidate pixel units in the cheek region 702, the mobile phone may connect a plurality of candidate pixel units adjacent to each other to obtain one or more candidate color spot regions in the face image 701. A facial color spot is generally round, and a size of the color spot is usually within a specific range. Therefore, after obtaining the candidate color spot region, the mobile phone may delete a candidate color spot region whose area is greater than a threshold 1 and less than a threshold 2 (the threshold 1 is greater than the threshold 2) or whose shape is irregular. In this case, one or more remaining candidate color spot regions are the color spot regions in the face image 701.

S403. The mobile phone displays a first interface including the face image, and prompts, in the first interface, the user that a color spot problem appears on a face.

Figure 8A:
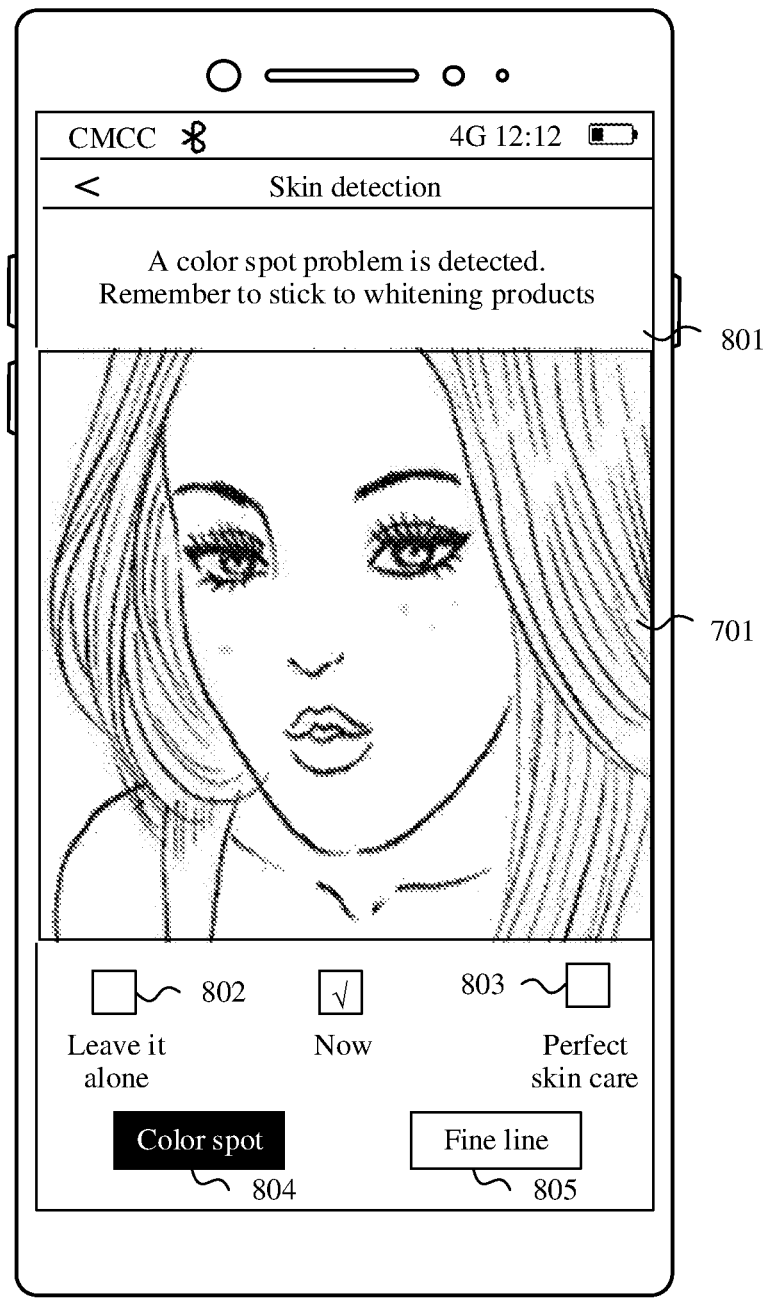
FIG. 8(a) and FIG. 8(b) are a schematic diagram 4 of a scenario of a skin detection method according to an embodiment of this application.
Figure 8B:
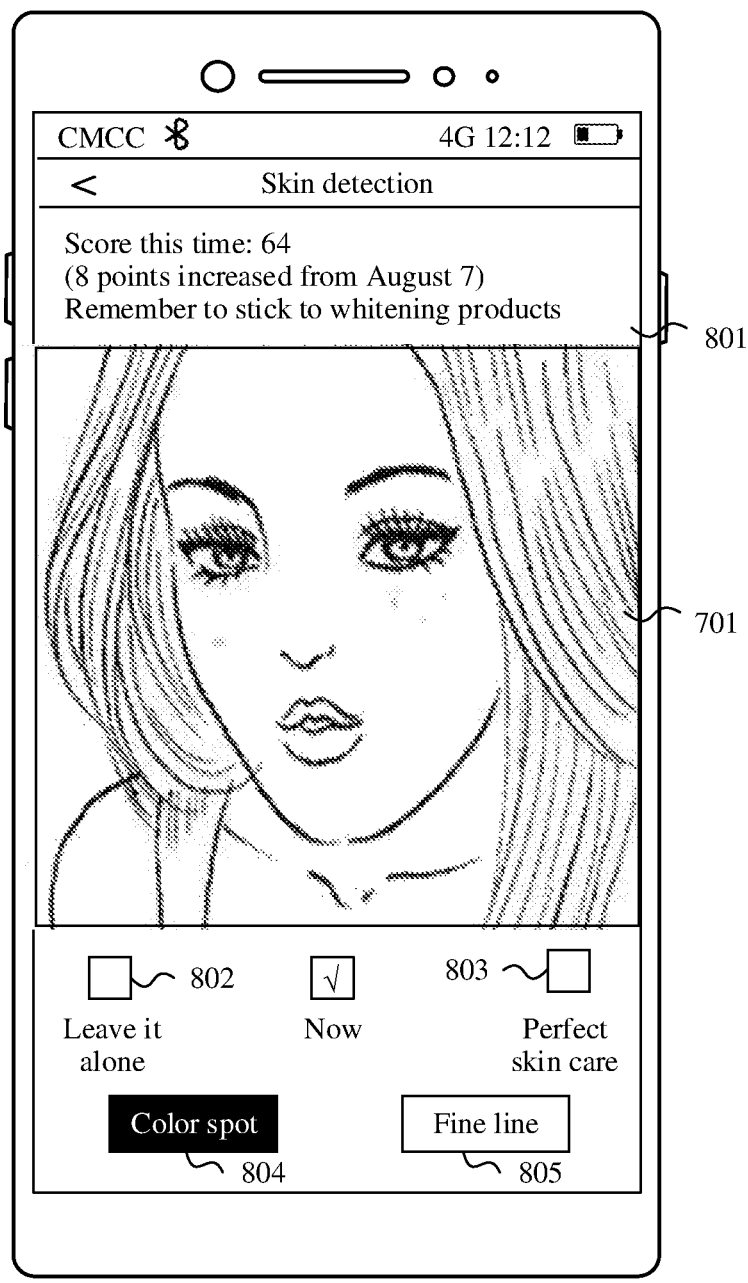

Still using the face image 701 as an example, if the mobile phone determines one or more color spot regions existing in the face image 701, as shown in FIG. 8(a) and FIG. 8(b), the mobile phone may display a first interface 801 including the face image 701. In addition, the mobile phone may prompt, in the first interface 801, the user that the color spot problem exists on the face.

For example, as shown in FIG. 8(a), the mobile phone may prompt, in the first interface 801 by using a text, the user that the color spot problem exists on the user's face. Alternatively, the mobile phone may further mark the determined color spot region in the face image 701 of the first interface 801, to help the user quickly find a position at which a color spot appears on the face. In addition, the mobile phone may further recommend a corresponding skin care suggestion to the user in the first interface 801. For example, for the color spot problem, the mobile phone may prompt the user to enhance sun protection or use a whitening and spot-removing product.

Figure 9:
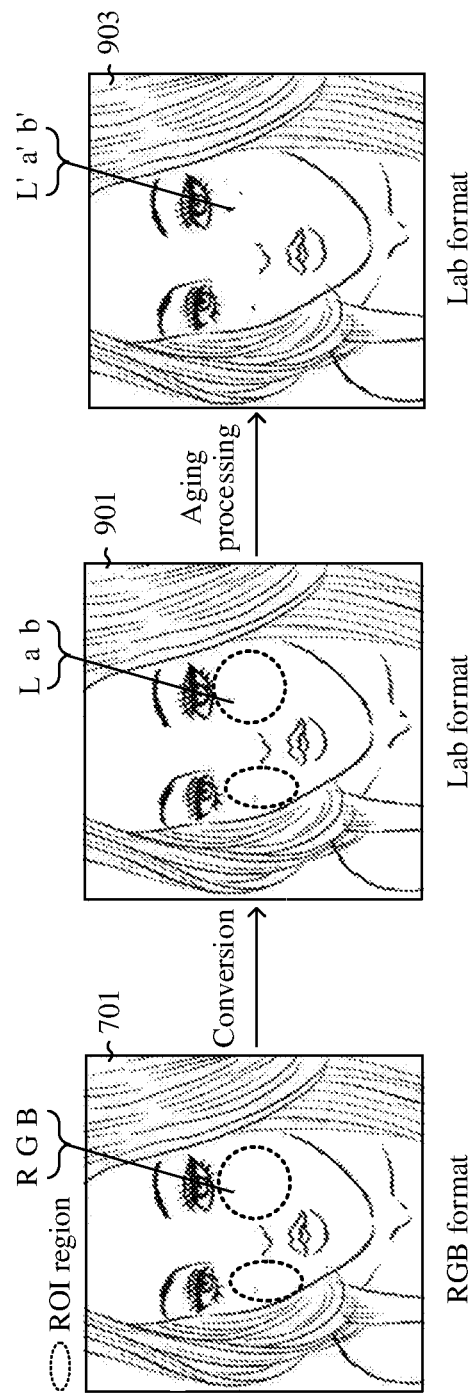
FIG. 9 is a schematic diagram 5 of a scenario of a skin detection method according to an embodiment of this application.

For another example, the mobile phone may further score the color spot problem on the user's face based on parameters such as a size, a quantity, and color darkness/lightness of the determined color spot region. A full score of 100 is used as an example, and a higher score indicates a more severe current color spot problem. As shown in FIG. 9, the mobile phone may display a current scoring status of the color spot problem in the first interface 801, to intuitively remind the user to pay attention to the color spot problem appearing on the face by using a score level, and perform timely repair.

Further, the mobile phone may further record scoring statuses of the color spot problem at a latest skin detection or latest skin detections. For example, the mobile phone scores the color spot problem with 64 points at a current skin detection by the user and scores the color spot problem with 56 points at a last skin detection by the user. In this case, still as shown in FIG. 8(b), the mobile phone may display a last score of the color spot problem, and the user is prompted that the current test result is 8 points higher than the last test result, so as to prompt the user to learn about a skin status change through scoring.

Certainly, if the mobile phone determines, in step S402, that the face image of the user does not include the color spot region, it indicates that no color spot problem appears on the skin of the user. The mobile phone may also prompt, in the first interface, the user that there is no color spot problem on the face. Alternatively, if the mobile phone detects, based on the obtained face image, another problem existing on the user's face, for example, a skin problem such as a blackhead, acne, or a fine line, the mobile phone may also prompt, in the first interface, the user that the skin problem is detected. This is not limited in this embodiment of this application.

For example, still as shown in FIG. 8(a) or FIG. 8(b), the first interface 801 may further include an aging button 802 and a de-aging button 803 for the color spot problem in the face image 701. If it is detected that the user taps the aging button 802, the mobile phone may perform the following step S404 to simulate an aging status of the facial color spot region of the user without skin care. Correspondingly, if it is detected that the user taps the de-aging button 803, the mobile phone may perform the following step S405 to simulate an improvement status of the facial color spot region of the user in the case of effective skin care, so as to intuitively remind the user about changes of the facial color spot region in different cases, thereby improving user experience of the user.

S404. If a first operation of the user in the first interface is detected, the mobile phone displays a second interface, where the second interface includes a face image obtained after the color spot region is aged.

For example, the first operation may be an operation of tapping the aging button 802 in the first interface 801 by the user. Certainly, the first operation may alternatively be an operation such as sliding or pressing by the user in the first interface 801. This is not limited in this embodiment of this application.

The mobile phone generally uses an RGB encoding format when obtaining the face image 701. Therefore, the face image 701 in the first interface 801 is usually an RGB format image. If it is detected that the user taps the aging button 802 in the first interface 801, as shown in FIG. 9, the mobile phone may convert the face image 701 in an RGB format into a face image 901 in a Lab format. Each pixel unit in the face image 901 includes three independent pixel channels L, a, and b, and each pixel channel has a corresponding pixel value (for example, a pixel value of the L pixel channel is L, a pixel value of the a pixel channel is a, and a pixel value of the b pixel channel is b). In addition, a ROI region (namely, a cheek region) in the face image 901 corresponds to the ROI region in the face image 701.

In this case, the mobile phone may calculate a change coefficient K1 of the L pixel channel, a change coefficient K2 of the a pixel channel, and a change coefficient K3 of the b pixel channel in the color spot region based on the pixel values of the three pixel channels L, a, and b of each pixel unit in the cheek region. Further, the mobile phone may update pixel values of three pixel channels L, a, and b of each pixel unit in the color spot region by using the change coefficients K1, K2, and K3, to implement aging processing on the color spot region.

For example, the mobile phone may calculate an average value $M_L$ of pixel values of all L pixel channel in the cheek region 902. In addition, the mobile phone may set a sliding window whose size is n×n in the cheek region 902, and a size of the sliding window is generally less than a size of the ROI (that is, the cheek region 902). Further, the mobile phone may move the sliding window within the cheek region 902 at a specific step, and there may be an overlapping area between two adjacent sliding windows. Each time after the sliding window is moved, if a current sliding window does not include a pixel unit in the color spot region, the mobile phone may continue to move the sliding window to a next position.

If a current sliding window includes one or more pixel units in the color spot region, the mobile phone may calculate an average value $j_L$ and a variance $f_L$ of pixel values of all L pixel channels located in the color spot region in the current sliding window, and an average value $m_L$ of pixel values of all L pixel channel in the current sliding window. Further, the mobile phone may calculate the change coefficient K1 of the L pixel channel in the current sliding window, where $K1=M_L/f_L \times (m_L-j_L)$. It can be learned that when a difference between the pixel average value $j_L$ of the color spot region in the sliding window and the pixel average value mL of the entire sliding window is smaller, which indicates that the color spot region in the current window is less obvious, a value of the change coefficient K1 is accordingly smaller. When a difference between the pixel average value $j_L$ of the color spot region in the sliding window and the pixel average value mL of the entire sliding window is larger, which indicates that the color spot region in the current window is more obvious, a value of the change coefficient K1 is accordingly larger.

Further, the mobile phone may perform aging processing on each L pixel channel in the color spot region in the current sliding window based on the change coefficient K1. For example, the mobile phone may update the pixel value L of the L pixel channel in the color spot region in the current sliding window to L' according to the following formula (1), where L' is in a positive correlation with the change coefficient K1.

$$L'=L+K1\times C1\times L \qquad \text{Formula (1)}$$

Herein, C1 is a preset constant.

Similarly, when the mobile phone moves the sliding window to the next position, the mobile phone may also update a pixel value of each L pixel channel in a corresponding color spot region according to the foregoing method. After the sliding window traverses the entire cheek region 902, as shown in FIG. 9, after aging processing is performed on each L pixel channel located in the color spot region in the cheek region, the pixel value of the L pixel channel is updated to L'.

It can be learned that when the value of the change coefficient K1 is larger, a corresponding color spot region is more obvious, and the updated value of L' calculated by using formula (1) is larger, so that a color of the color spot region after the aging processing becomes yellower, thereby implementing a visual effect of color spot aging.

In some embodiments, a coefficient threshold (for example, P1) of L pixel channels may be set in the mobile phone in advance. After calculating pixel values L' of the L pixel channels in the color spot region in the current sliding window, the mobile phone may further calculate an average value of updated values L'. If the average value of L' is less than the coefficient threshold P1, it indicates that the L pixel channels in the current color spot region change very little, and it is difficult for the user to distinguish such a slight change by a naked eye. Therefore, the mobile phone may continue to update the pixel values of the L pixel channels in the color spot region by using the foregoing formula (1) until an average value of updated pixel values of the L pixel channels is greater than or equal to the coefficient threshold P1.

Similarly, the mobile phone may further calculate the change coefficient K2 of the a pixel channel in each sliding window according to the foregoing method. $K2=M_a/f_a \times (m_a-j_a)$, where $M_a$ is an average value of pixel values of all a pixel channels in the cheek region, and $m_a$ is an average value of pixel values of all a pixel channels in the sliding window, $j_a$ is an average value of pixel values of all a pixel channels in the color spot region in the sliding window, and $f_a$ is a variance of the pixel values of all a pixel channels in the color spot region in the sliding window.

Further, the mobile phone may perform aging processing on the a pixel channel in the color spot region in each sliding window based on the change coefficient K2. For example, as shown in FIG. 9, the mobile phone may update a pixel value a of each a pixel channel in the color spot region in the sliding window to a' according to the following formula (2), where a' is in a positive correlation with the change coefficient K2.

$$a'=a+K2 \times C2 \times a \qquad \text{Formula (2)}$$

Herein, C2 is a preset constant.

Similarly, a coefficient threshold (for example, P2) of a pixel channels may be set in the mobile phone in advance. After calculating pixel values a' of the a pixel channels in the color spot region in the current sliding window, the mobile phone may further calculate an average value of updated values a'. If the average value of a' is less than the coefficient threshold P2, it indicates that the a pixel channels in the current color spot region change very little, and it is difficult for the user to distinguish such a slight change by a naked eye. Therefore, the mobile phone may continue to update the pixel values of the a pixel channels in the color spot region by using the foregoing formula (2) until an average value of updated pixel values of the a pixel channels is greater than or equal to the coefficient threshold P2.

Similarly, the mobile phone may further calculate the change coefficient K3 of the b pixel channel in each sliding window according to the foregoing method. $K3=M_b/f_b \times (m_b-j_b)$, where Mb is an average value of pixel values of all b pixel channels in the cheek region, $m_b$ is an average value of pixel values of all b pixel channels in the sliding window, jb is an average value of pixel values of all b pixel channels in the color spot region in the sliding window, and fb is the variance of the pixel values of all b pixel channels in the color spot region in the sliding window.

Further, the mobile phone may perform aging processing on the b pixel channel of the color spot region in each sliding window based on the change coefficient K3. For example, as shown in FIG. 9, the mobile phone may update a pixel value b of each b pixel channel in the color spot region in the sliding window to b' according to the following formula (3), where b' is in a positive correlation with the change coefficient K3.

$$b'=b+K3 \times C3 \times b \qquad \text{Formula (3)}$$

Herein, C3 is a preset constant.

Similarly, a coefficient threshold (for example, P3) of b pixel channels may be set in the mobile phone in advance. After calculating pixel value b' of the b pixel channels in the color spot region in the current sliding window, the mobile phone may further calculate an average value of updated values b'. If the average value of b' is less than the coefficient threshold P3, it indicates that the b pixel channels in the current color spot region change very little, and it is difficult for the user to distinguish such a slight change by a naked eye. Therefore, the mobile phone may continue to update the pixel values of the b pixel channels in the color spot region by using the foregoing formula (3) until an average value of updated pixel values of the b pixel channels is greater than or equal to the coefficient threshold P3.

In this way, as shown in FIG. 9, the mobile phone may perform aging processing on the color spot region in the face image 901 based on the change coefficients K1, K2, and K3, to obtain an aged face image 903. In the face image 903, a change coefficient determined by the mobile phone for a region with a relatively obvious color spot is relatively large, so that a pixel value of each pixel channel determined by the mobile phone according to the foregoing formulas (1) to (3) is also relatively large, that is, a color of a color spot in this region after the aging becomes yellower, thereby implementing a visual effect of color spot enhancement.

It should be noted that, the method for performing aging processing on the color spot region by the mobile phone in the foregoing embodiment is merely an example for description, and a person skilled in the art may set the method based on an actual application scenario or actual experience. For example, the mobile phone may set a fixed change coefficient K1 for the L pixel channel, a fixed change coefficient K2 for the a pixel channel, and a fixed change coefficient K3 for the b pixel channel, and then use the change coefficients K1, K2, and K3 to calculate each pixel value of an aged color spot region. This is not limited in this embodiment of this application.

Figure 10:
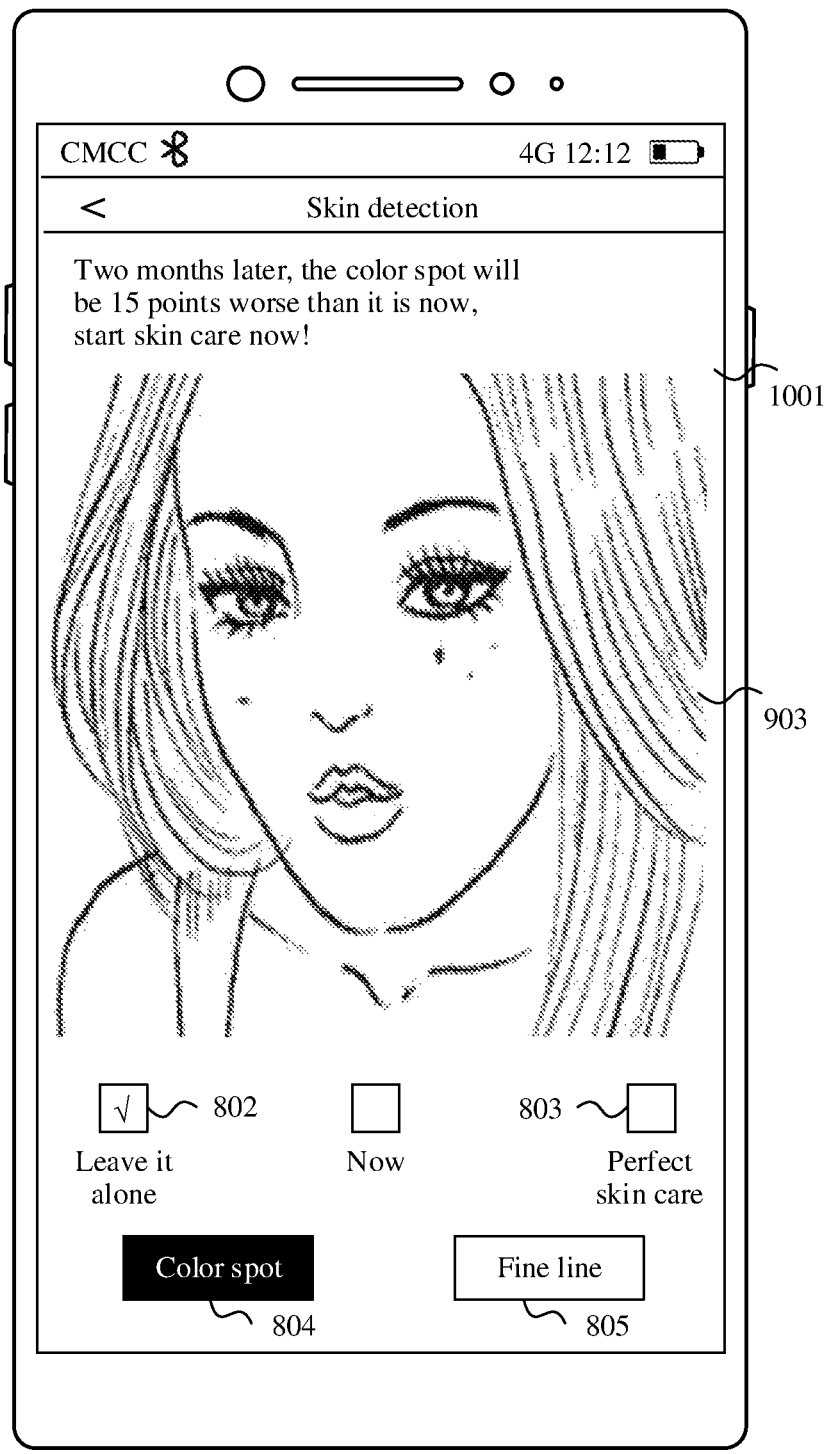
FIG. 10 is a schematic diagram 6 of a scenario of a skin detection method according to an embodiment of this application.

In addition, after the mobile phone determines the aged face image 903, as shown in FIG. 10, the mobile phone may display the face image 903 in the second interface 1001. In this embodiment of this application, a face image that is simulated by the mobile phone and that is obtained after aging of the color spot region may be referred to as a facial simulated image (for example, a first facial simulated image). For example, the mobile phone may display the face image 903 in the Lab format in the second interface 1001, or may display the face image 903 in the RGB format in the second interface 1001. This is not limited in this embodiment of this application. In some embodiments, the mobile phone may further perform smoothing filtering processing on the aged face image 903, so that a color spot boundary in the face image 903 achieves smooth transition. In the second interface 1001, the user may intuitively view the face image obtained after the color spot problem is aged, so as to remind the user to repair the color spot problem on the face in a timely manner.

In addition, the mobile phone may further prompt, in the second interface 1001, the user that the currently displayed face image 903 is a schematic diagram of a facial effect when the color spot is not repaired for a period of time (for example, two months). In addition, the mobile phone may further score the color spot problem in the aged face image 903, and display a score result in the second interface 1001, to remind the user to repair the color spot problem on the face in a timely manner.

Figure 11:
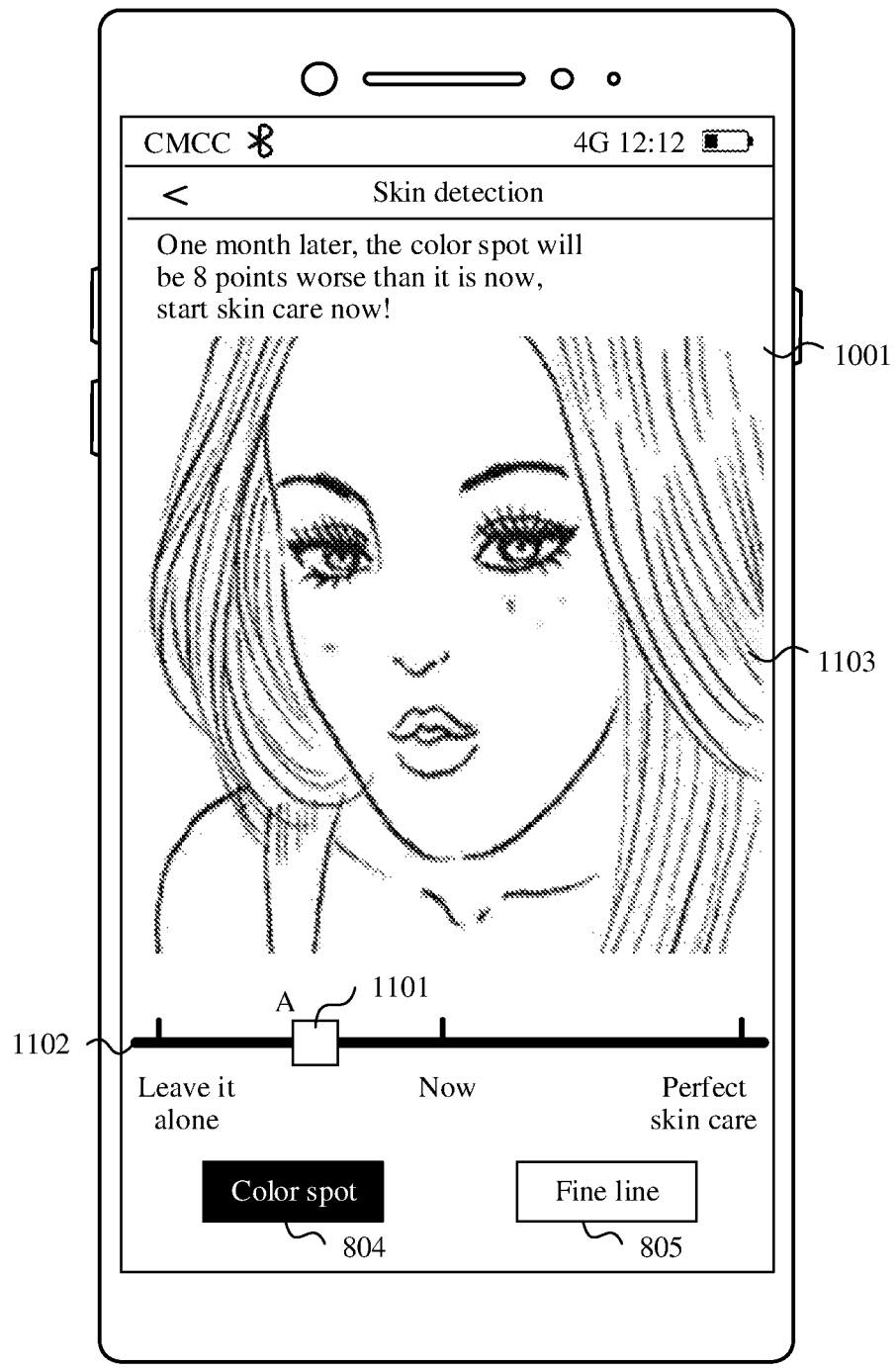
FIG. 11 is a schematic diagram 7 of a scenario of a skin detection method according to an embodiment of this application.

For example, the mobile phone may further display, to the user in the second interface 1001, aging statuses of the color spot problem after different periods of time. As shown in FIG. 11, the user may drag a slider 1101 in the second interface 1001 to slide on an aging progress bar 1102. When the user drags the slider 1101 to an end point (namely, the aging button 802) of the aging progress bar 1102, the mobile phone may display the face image 903 obtained after the aging processing is performed. In this case, the displayed face image 903 is a skin status after the user has not repaired the color spot problem for two months.

If it is detected that the user drags the slider 1101 to a position close to the aging button 802, for example, as shown in FIG. 11, when the user drags the slider 1101 to a middle point A of the aging progress bar 1102, the mobile phone may recalculate an aging status of the color spot problem based on the position of the slider 1101. For example, the mobile phone may multiply a pixel value of each pixel unit calculated in FIG. 9 by a corresponding proportional coefficient w (0<w<1) based on the position of the slider 1101. For example, if a pixel value of an L pixel channel of a pixel unit 1 in the face image 903 is 160, a pixel value of an a pixel channel is 96, and a pixel value of a b pixel channel is 244, the mobile phone may determine, based on a position A of the slider 1101 on the aging progress bar 1102, a proportional coefficient w=0.5. Further, the mobile phone may calculate pixel values of the pixel unit 1 in the aged face image 1103 corresponding to the location A, which include: a pixel value of the L pixel channel 160×0.5=80, a pixel value of the a pixel channel 96×0.5=48, and a pixel value of the b pixel channel 244×0.5=122. Similarly, the mobile phone may calculate a pixel value of each pixel unit in the color spot region of the face image 1103. Further, as shown in FIG. 11, the mobile phone may display the face image 1103 in the second interface 1001 based on the calculated pixel values, so as to display, to the user, an aging status of the color spot problem one month later. To be specific, when the user drags the slider 1101 toward the aging button 802, the mobile phone may display, in a time sequence, aging statuses of the color spot problem of the user's face at different time points, so that the user can dynamically sense the aging status of the color spot problem on the current face over time.

S405. If a second operation of the user in the first interface is detected, the mobile phone displays a third interface, where the third interface includes a face image obtained after the color spot region is de-aged.

Step S404 describes the method for performing de-aging processing on the color spot region. Correspondingly, step S405 describes a method for performing aging processing on the color spot region. In other words, the skin detection method provided in this embodiment of this application can be used to simulate a change in aging of user skin in a period of time, and may also simulate a change in de-aging of user skin in a period of time.

For example, the second operation may be an operation of tapping the de-aging button 803 in the first interface 801 in FIG. 8(a) and FIG. 8(b) by the user. Certainly, the second operation may alternatively be an operation such as sliding or pressing by the user in the first interface 801. This is not limited in this embodiment of this application.

Similar to step S404, still as shown in FIG. 9, after it is detected that the user performs the second operation in the first interface 801, the mobile phone may convert the face image 701 in the RGB format into the face image 901 in the Lab format. A ROI region (namely, the cheek region) in the face image 901 corresponds to the ROI region in the face image 701. Further, the mobile phone may separately calculate a change coefficient K1 of the L pixel channel, a change coefficient K2 of the a pixel channel, and a change coefficient K3 of the b pixel channel based on the pixel values of three pixel channels L, a, and b in each pixel unit in the cheek region. A method for calculating the change coefficients K1, K2, and K3 is the same as the method for calculating the change coefficients K1, K2, and K3 in step S404. Therefore, details are not described herein again.

Different from step S404, the mobile phone may separately perform de-aging processing on each L pixel channel, a pixel channel, and b pixel channel in the color spot region based on the change coefficients K1, K2, and K3.

For example, the mobile phone may update a pixel value L of each L pixel channel in the color spot region to L' according to the following formula (4), where L' is in a negative correlation with the change coefficient K1, and formula (4) is: L'=L−K1×C1×L.

Similarly, the mobile phone may update a pixel value a of each a pixel channel in the color spot region to a' according to the following formula (5), where a' is in a negative correlation with the change coefficient K2, and formula (5) is: a'=a−K2×C2× a.

Similarly, the mobile phone may update a pixel value b of each b pixel channel in the color spot region to b' according to the following formula (6), where b' is in a negative correlation with the change coefficient K3, and formula (6) is: b'=b−K3×C3×b.

Figure 12:
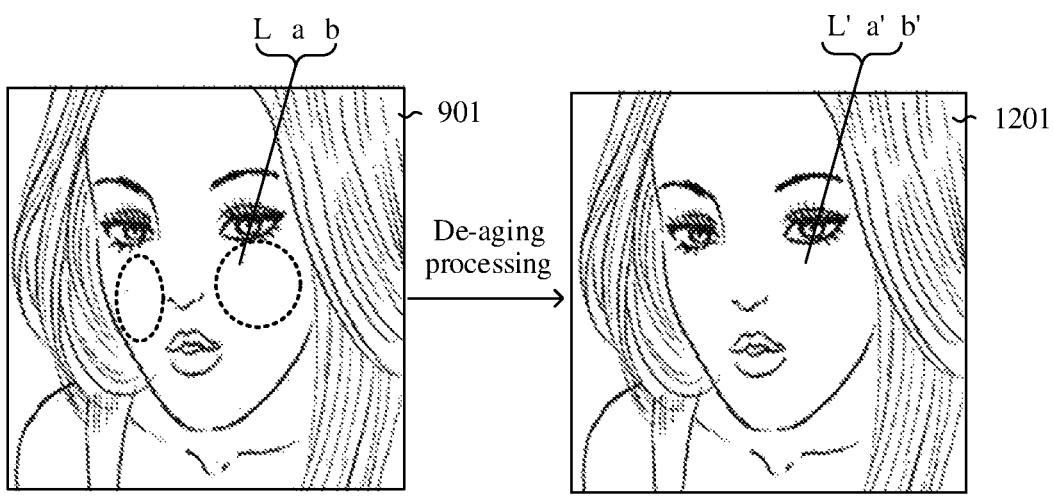
FIG. 12 is a schematic diagram 8 of a scenario of a skin detection method according to an embodiment of this application.

In this way, as shown in FIG. 12, the mobile phone performs de-aging processing on the color spot region of the face image 901 based on the change coefficients K1, K2, and K3 to obtain a face image 1201. In the face image 1201, a change coefficient determined by the mobile phone for an area with a relatively obvious color spot is relatively large, so that pixel values of pixel channels determined by the mobile phone according to the foregoing formulas (4) to (6) are relatively small, that is, a color of the color spot region becomes light after the de-aging, thereby implementing a visual effect of color spot lightening.

Figure 13A:
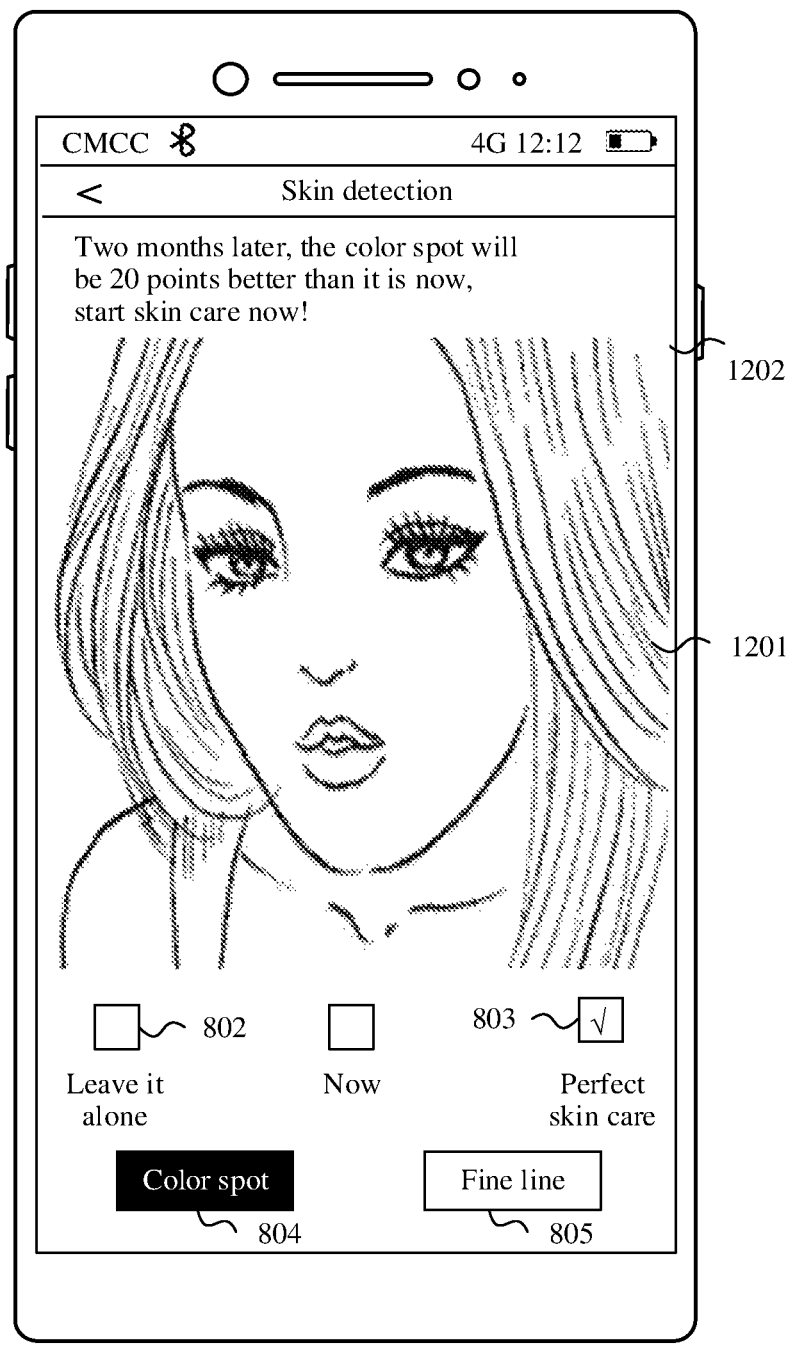
FIG. 13(a) and FIG. 13(b) are a schematic diagram 9 of a scenario of a skin detection method according to an embodiment of this application.

As shown in FIG. 13(a), the mobile phone may display, in the third interface 1202, the face image 1201 obtained after the color spot region is de-aged, so that the user can intuitively view, in the second interface 1001, the face image obtained after the color spot problem is de-aged, so as to remind the user to repair, in a timely manner, the color spot problem that appears on the face. In this embodiment of this application, a face image that is simulated by the mobile phone and that is obtained after the color spot region is de-aged may be referred to as a facial simulated image (for example, a second facial simulated image). Certainly, the mobile phone may further display, in the third interface 1202, a scoring status of the color spot problem in the face image 1201.

Figure 13B:
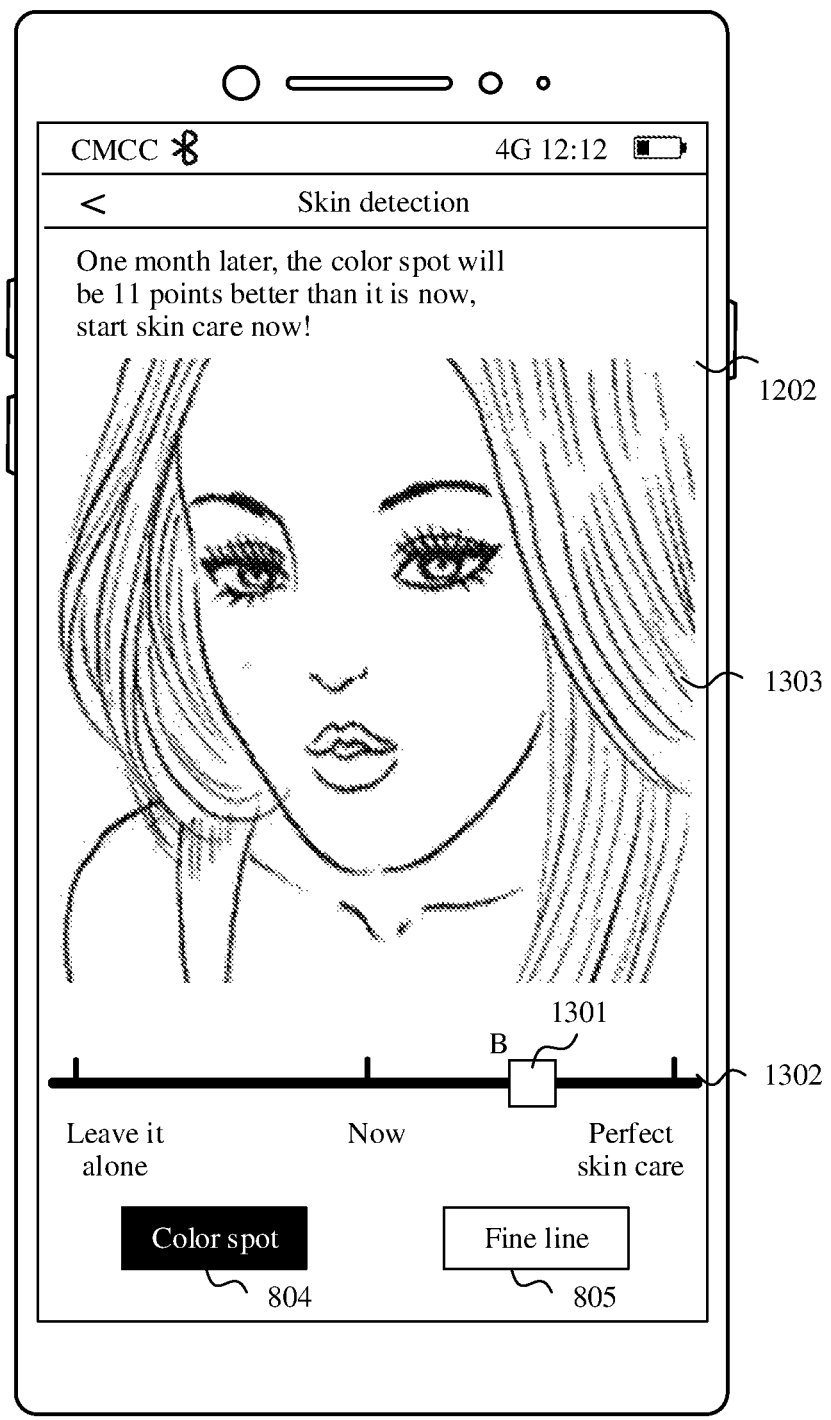

In some embodiments, the mobile phone may further display, to the user in the third interface 1202, de-aging statuses of the color spot problem after different periods of time. As shown in FIG. 13(b), the user may drag a slider 1301 in the third interface 1202 to slide on a de-aging progress bar 1302. When the user drags the slider 1301 to an end point (namely, the de-aging button 803) of the aging progress bar 1302, the mobile phone may display the de-aged face image 1201. For example, the face image 1201 is a skin status two months after the user repairs the color spot problem.

If it is detected that the user drags the slider 1301 to a position close to the de-aging button 803, for example, as shown in FIG. 13(*a*) and FIG. 13(*b*), when the user drags the slider 1301 to a middle point B of the de-aging progress bar 1302, the mobile phone may recalculate a de-aging status of the color spot problem based on a position of the slider 1301. For example, the mobile phone may multiply a pixel value of each pixel unit in the color spot region of the face image 1201 by a corresponding proportional coefficient w (0<w<1) based on the position of the slider 1301. Further, as shown in FIG. 13(*a*) and FIG. 13(*b*), the mobile phone may display a face image 1303 in the second interface 1001 based on each calculated pixel value. For example, the face image 1303 is a skin status one month after the user repairs the color spot problem. In other words, when the user drags the slider 1301 toward the de-aging button 803, the mobile phone may display, in a time sequence, de-aging statuses of the color spot problem on the user's face at different time points, so that the user can dynamically sense the de-aging status of the color spot problem on the current face over time.

Figure 14:
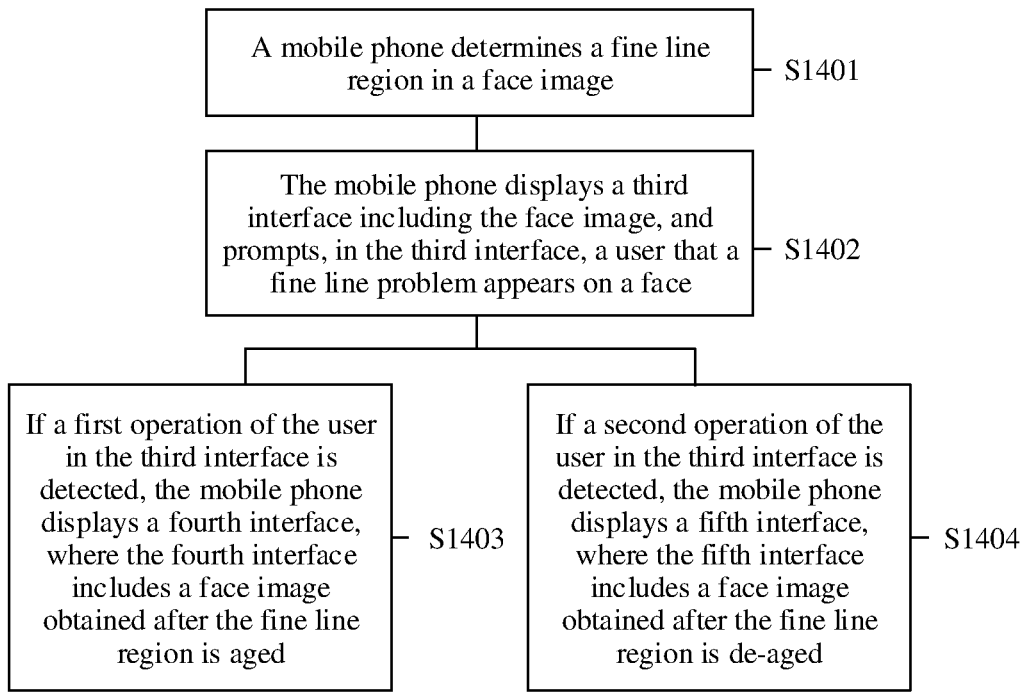
FIG. 14 is a schematic flowchart 2 of a skin detection method according to an embodiment of this application.

The foregoing embodiment is described by using an example in which the mobile phone simulates an aging scenario and a de-aging scenario of the color spot problem in the face image of the user. It may be understood that after obtaining the face image (for example, the face image 701) of the user, the mobile phone may further detect another problem that appears on the user's face. As shown in FIG. 14, in the following embodiment, detection of a fine line problem that appears on the user's face is used as an example for description.

S1401. The mobile phone determines a fine line region in the face image.

After obtaining the face image of the user, the mobile phone may extract, by using a preset fine line detection algorithm, a fine line region in which a fine line exists from the face image. Still as shown in FIG. 8(*a*) and FIG. 8(*b*), when displaying the first interface 801 including the face image 701, the mobile phone further sets a color spot button 804 and a fine line button 805 in the first interface 801. If it is detected that the user taps the fine line button 805, the mobile phone may extract the fine line region in which the fine line exists from the face image. Alternatively, after obtaining the face image 701, the mobile phone may automatically extract the fine line region in which the fine line exists from the face image. This is not limited in this embodiment of this application.

The fine line detection algorithm may be a spiral pyramid algorithm or the like. A person skilled in the art may set the fine line detection algorithm based on actual experience or an actual application scenario. This is not limited in this embodiment of this application.

S1402. The mobile phone displays a third interface including the face image, and prompts, in the third interface, the user that a fine line problem appears on the face.

Figure 15:
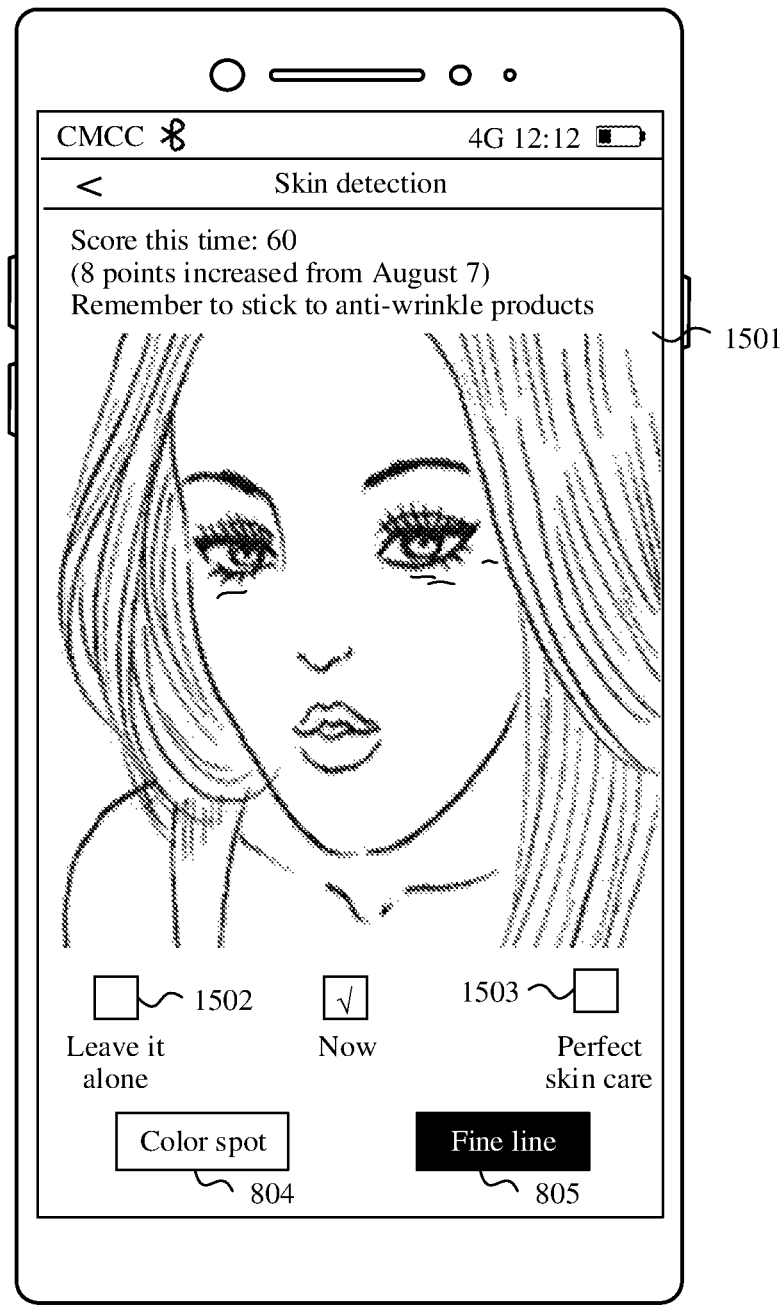
FIG. 15 is a schematic diagram 10 of a scenario of a skin detection method according to an embodiment of this application.

Similar to step S403, after the mobile phone determines the fine line region in the face image 701, as shown in FIG. 15, the mobile phone may display the face image of the user in the third interface 1501, and prompt, in the third interface 1501, the user that the fine line problem exists on the face. For example, the mobile phone may mark the determined fine line region in the face image 1501 of the third interface 1501. For another example, the mobile phone may score the fine line problem that appears in the face image 1501, and display a scoring result in the third interface 1501. For another example, the mobile phone may further display, in the third interface 1501, a corresponding skin care suggestion recommended to the user, for example, enhancing water replenishment or using a wrinkle-removing product.

For example, as shown in FIG. 15, the third interface 1501 may further include an aging button 1502 and a de-aging button 1503 for the fine line problem in the face image 701. If it is detected that the user taps the aging button 1502, the mobile phone may perform the following step S1403 to simulate an aging status of the fine line region of the user's face without skin care. Correspondingly, if it is detected that the user taps the de-aging button 1503, the mobile phone may perform the following step S1404 to simulate an improvement status of the facial fine line region of the user in the case of effective skin care, so as to intuitively remind the user about changes of the facial fine line region in different cases, thereby improving user experience of the user.

S1403. If a first operation of the user in the third interface is detected, the mobile phone displays a fourth interface, where the fourth interface includes a face image obtained after the fine line region is aged.

For example, if it is detected that the user taps the aging button 1502 in the third interface 1501, it indicates that the user expects to view the aged fine line region. Fine line aging reflected on an image generally means that a fine line color deepens and darkens. Therefore, the mobile phone may perform darkening processing on a pixel unit of the determined fine line region.

For example, the mobile phone may convert the face image 701 in the RGB format into a face image 1601 in the grayscale format. Each pixel unit in the face image 1601 has a grayscale value G. The mobile phone may determine a change coefficient D of the fine line region based on the grayscale value G of each pixel unit.

For example, the mobile phone may perform normalization processing on grayscale values of pixel units in the face image 1601, and then the mobile phone may calculate a grayscale average value $G_p$ of normalized pixel units in the face image 1601. The mobile phone may set the change coefficient D to: D=Gp+C4, where C4 is a constant, for example, C4=0.5.

Figure 16:
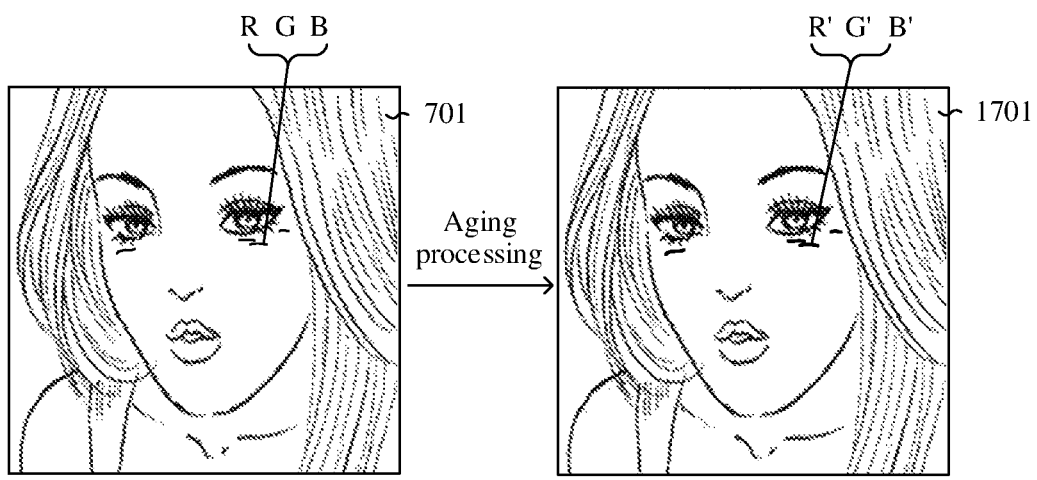
FIG. 16 is a schematic diagram 11 of a scenario of a skin detection method according to an embodiment of this application.

After the mobile phone determines the change coefficient D of the fine line region, as shown in FIG. 16, the mobile phone may modify pixel values of R, G, and B pixel channels of the fine line region in the face image 701, so that the fine line color deepens and darkens. For example, an updated value of the R pixel channel is R'=R−C5×D, where C5 is a constant (for example, C5=0.229); an updated value of the G pixel channel is G'=G−C6×D, where C6 is a constant (for example, C6=0.587); an updated value of the B pixel channel is B'=B−C7×D, where C7 is a constant (for example, C7=0.114). It can be learned that an updated value of each pixel channel is in a negative correlation with the change coefficient D.

Figure 17:
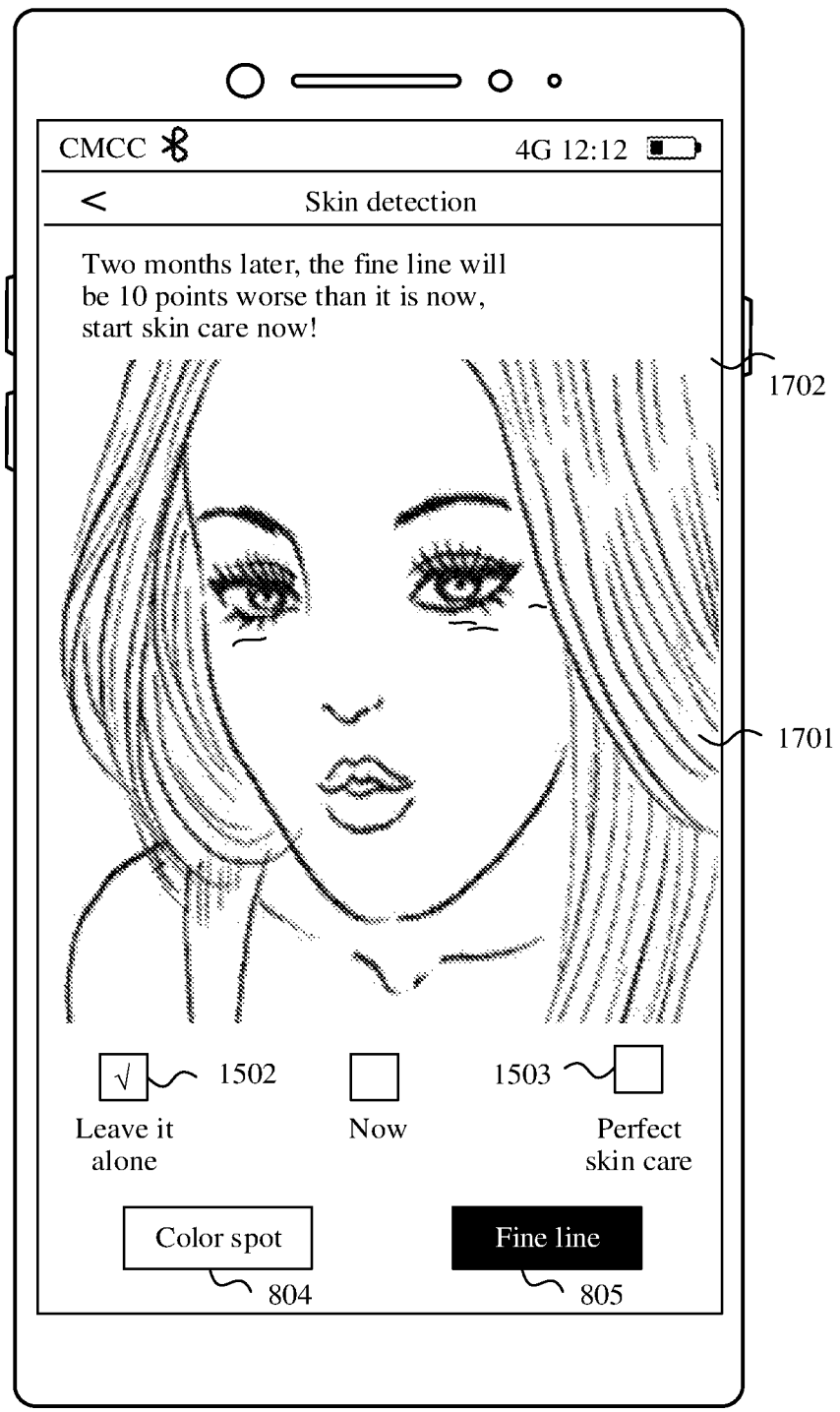
FIG. 17 is a schematic diagram 12 of a scenario of a skin detection method according to an embodiment of this application.

Further, as shown in FIG. 17, the mobile phone may display, in the fourth interface 1702, the face image 1701 obtained after the fine line region is updated. The face image 1701 may be referred to as a facial simulated image (for example, a first facial simulated image). In the face image 1701, the mobile phone decreases the pixel value of each pixel channel in the fine line region by using the foregoing formulas, so that the fine line region darkens and darkens, thereby simulating a visual effect of fine line aging.

Figure 18:
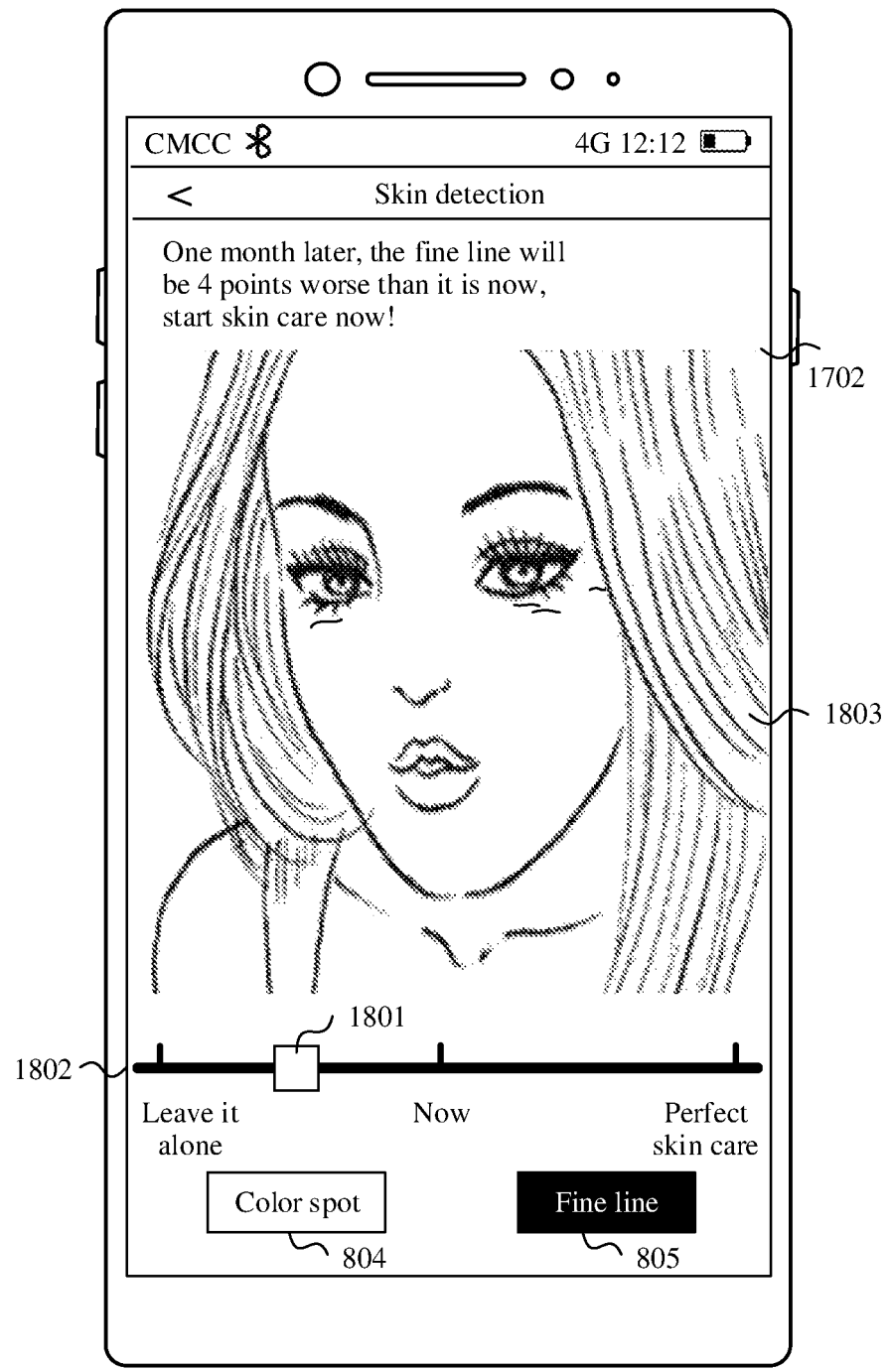
FIG. 18 is a schematic diagram 13 of a scenario of a skin detection method according to an embodiment of this application.

For example, the mobile phone may further display, to the user in the fourth interface 1702, aging statuses of the fine line problem after different periods of time. As shown in FIG. 18, the user may drag a slider 1801 in the fourth interface 1702 to slide on an aging progress bar 1802. When the slider 1801 is dragged to different positions, the mobile phone may display face images with aged fine lines after different periods of time, so that the user can dynamically sense the aging status of the fine line problem on the current face over time.

For example, when the user drags the slider 1801 to an end point (namely, the aging button 1502) of the aging progress bar 1802, the mobile phone may display an aged face image 1701, where the face image 1701 is a skin status after the user has not repaired the fine line problem for two months. When the user drags the slider 1801 to a middle position of the aging progress bar 1802, the mobile phone may multiply pixel values of R, G, and B pixel channels of the fine line region in the face image 1701 by a corresponding proportional coefficient v (0<v<1), to obtain a face image 1803 corresponding to the current slider position. As shown in FIG. 18, the face image 1803 is a skin status after the user has not repaired the fine line problem for one month.

S1404. If a second operation of the user in the third interface is detected, the mobile phone displays a fifth interface, where the fifth interface includes a face image obtained after the fine line region is de-aged.

For example, if it is detected that the user taps the de-aging button 1503 in the third interface 1501, it indicates that the user expects to view of the de-aged fine line region. Fine line de-aging reflected in an image generally means that a fine line color becomes lightened and brightened. Therefore, the mobile phone may perform lightening processing on a pixel unit of the determined fine line region.

Figure 19:
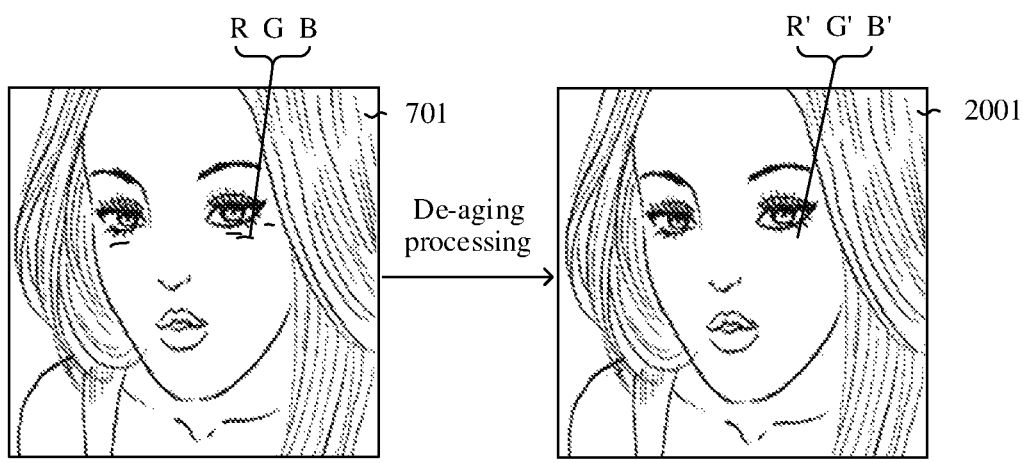
FIG. 19 is a schematic diagram 14 of a scenario of a skin detection method according to an embodiment of this application.

For example, the mobile phone may calculate the change coefficient D of the fine line region according to the method in step S1403. Further, as shown in FIG. 19, the mobile phone may modify the pixel values of the R, G, and B pixel channels of the fine line region in the face image 701, so that the fine line color becomes lightened and brightened. For example, an updated value of the R pixel channel is R'=R+C5×D; an updated value of the G pixel channel is G'=G+C6×D; an updated value of the B pixel channel is B'=B+C7×D. It can be learned that an updated value of each pixel channel is in a positive correlation with the change coefficient D.

Figure 20A:
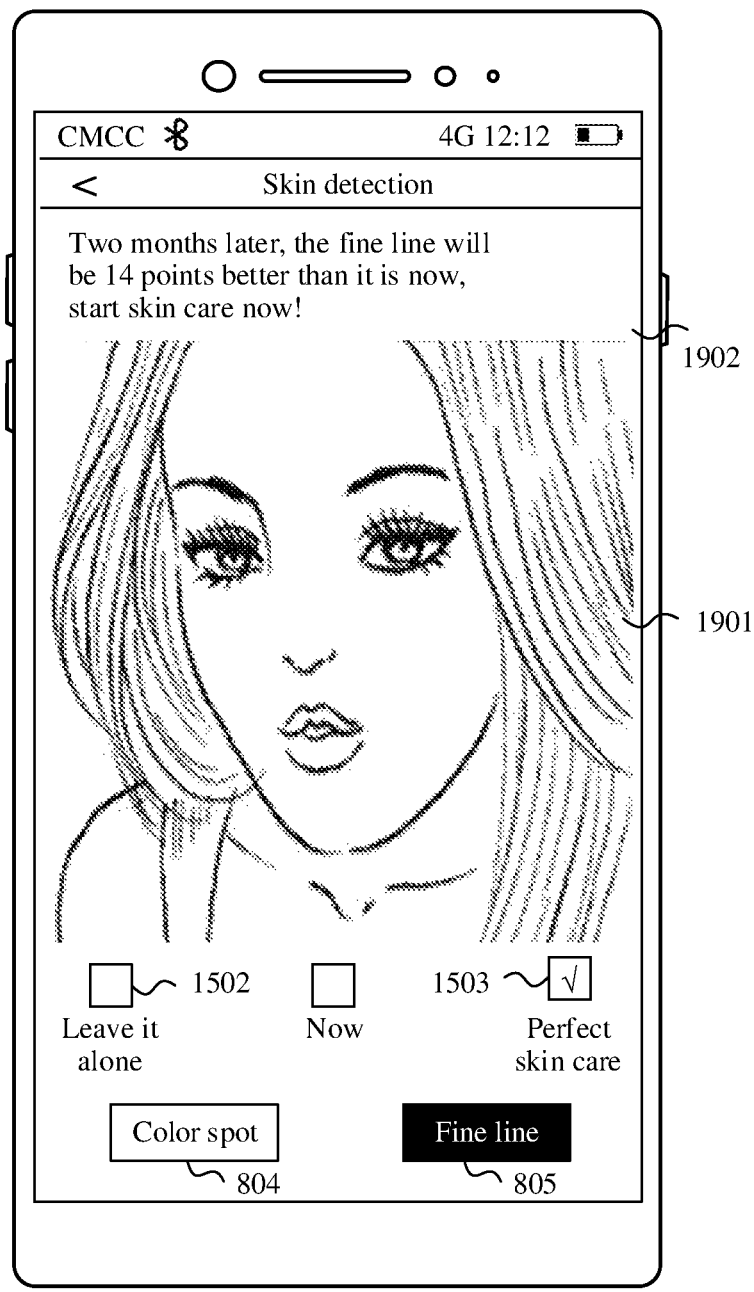
FIG. 20(a) and FIG. 20(b) are a schematic diagram 15 of a scenario of a skin detection method according to an embodiment of this application.

Further, as shown in FIG. 20(a), the mobile phone may display, in a fifth interface 1902, a face image 1901 obtained after the fine line region is updated. The face image 1901 may be referred to as a facial simulated image (for example, a second facial simulated image). In the face image 1901, the mobile phone increases a pixel value of each pixel channel in the fine line region by using the foregoing formulas, so that the fine line region becomes lightened and brightened, so as to simulate a visual effect of fine line de-aging.

Figure 20B:
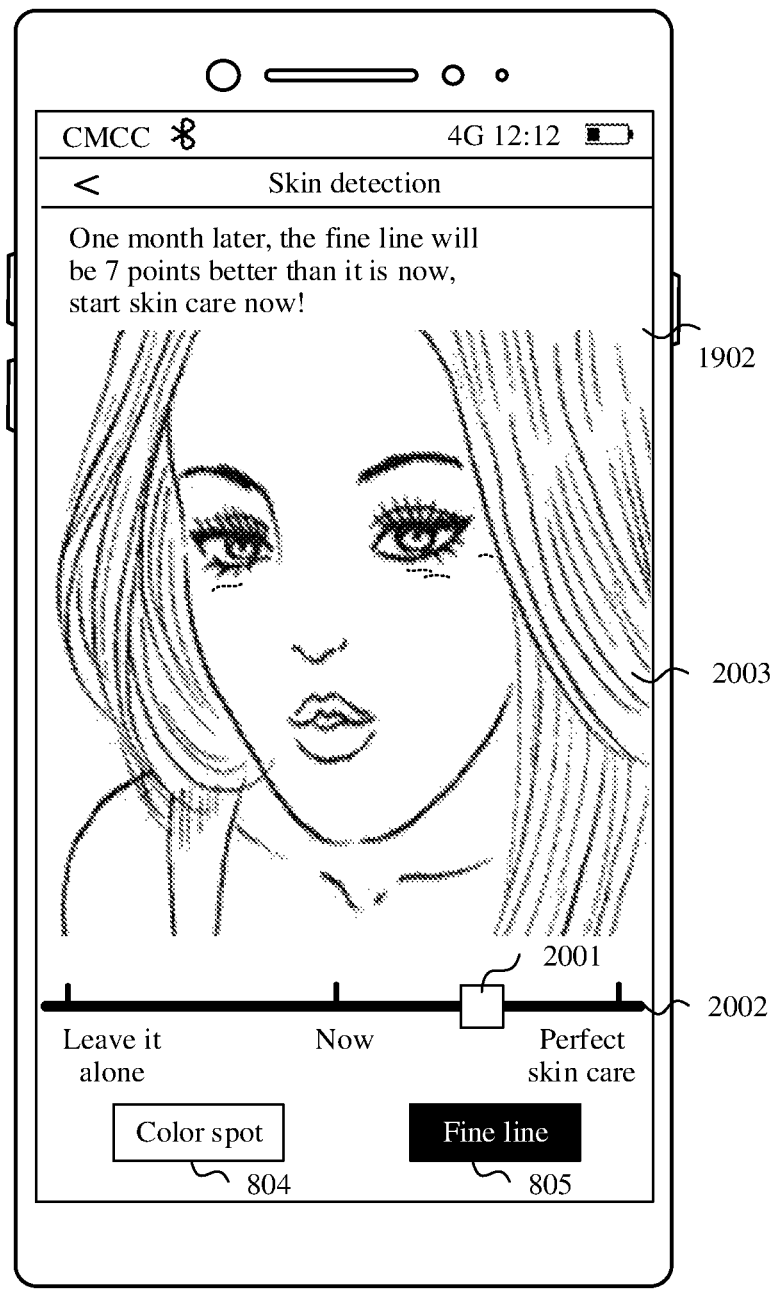

For example, the mobile phone may further display, to the user in the fifth interface 1902, aging statuses of the fine line problem after different periods of time. As shown in FIG. 20(b), the user may drag a slider 2001 in the fifth interface 1902 to slide on a de-aging progress bar 2002. When the slider 2001 is dragged to different positions, the mobile phone may display face images with de-aged fine lines after different periods of time, so that the user can dynamically sense the de-aging status of the fine line problem on the current face over time.

For example, when the user drags the slider 2001 to an end point of the de-aging progress bar 2002 (namely, the de-aging button 1503), the mobile phone may display the de-aged face image 1901, where the face image 1901 is a skin status two months after the user repairs the fine line problem. When the user drags the slider 2001 to a middle position of the de-aging progress bar 2002, the mobile phone may multiply pixel values of R, G, and B pixel channels of the fine line region in the face image 1901 by a corresponding proportional coefficient v (0<v<1), to obtain a face image 2003 corresponding to the current slider position. As shown in FIG. 20(b), the face image 2003 is a skin status one month after the user repairs the fine line problem.

Figure 21:
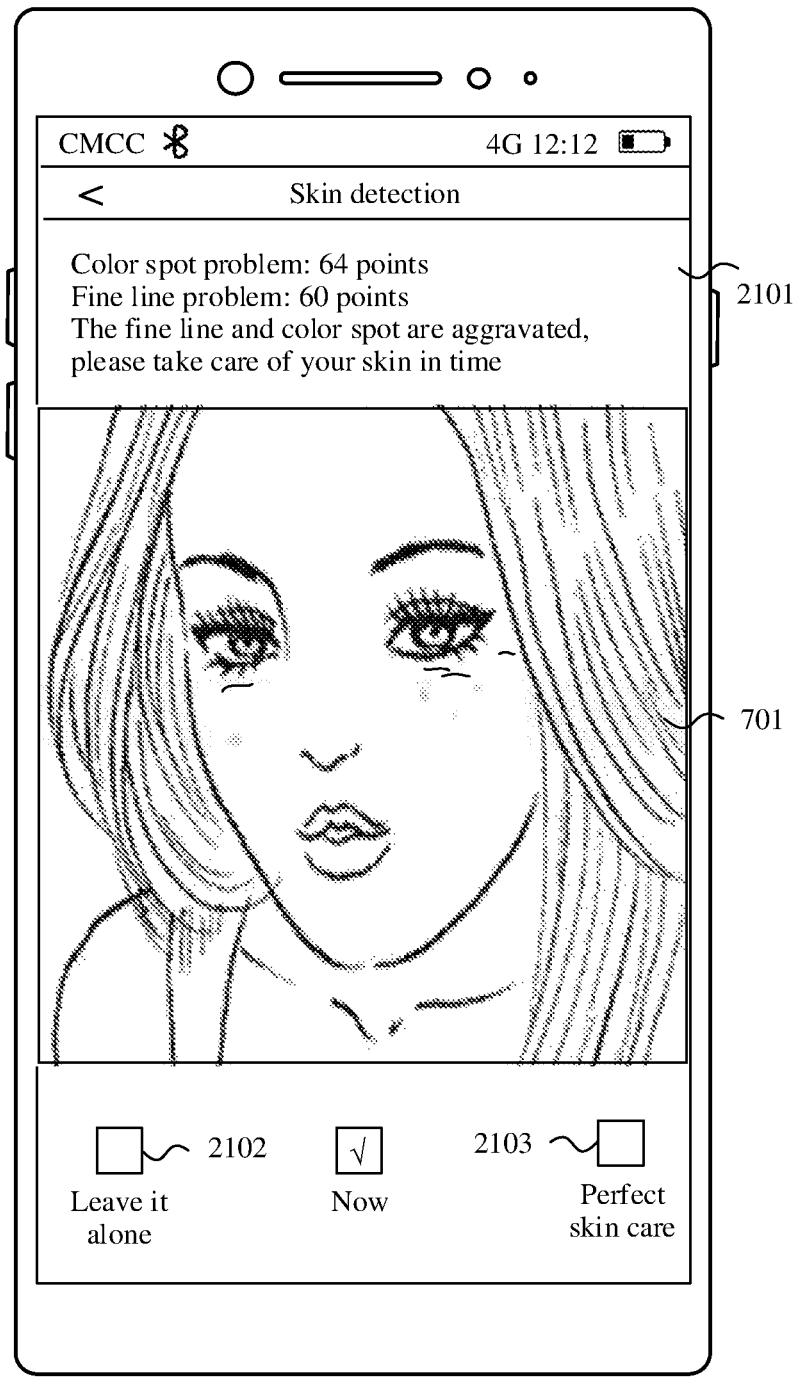
FIG. 21 is a schematic diagram 16 of a scenario of a skin detection method according to an embodiment of this application.

In some other embodiments, after obtaining the face image (for example, the face image 701) of the user, the mobile phone may not only determine a color spot region in the face image, but also determine a fine line region in the face image. Further, as shown in FIG. 21, when displaying the face image 701 of the user in an interface 2101, the mobile phone may prompt the user that both the color spot problem and the fine line problem appear on the face.

Figure 22A:
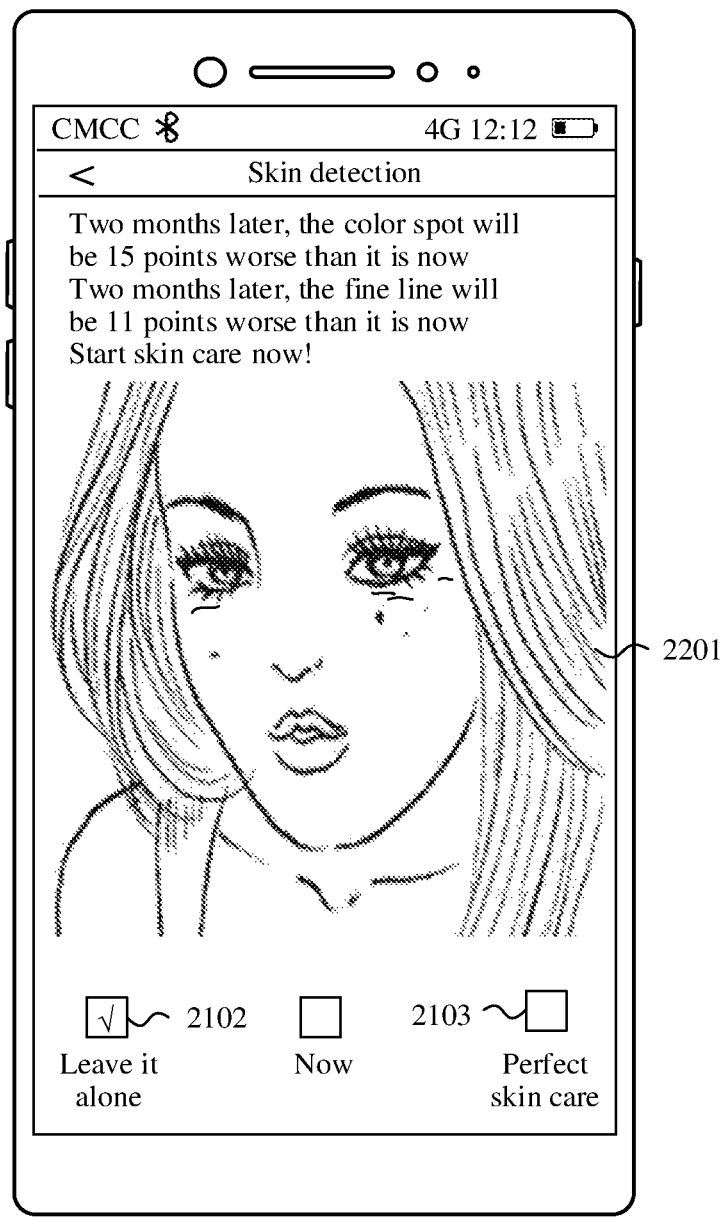
FIG. 22(a) and FIG. 22(b) are a schematic diagram 17 of a scenario of a skin detection method according to an embodiment of this application.
Figure 22B:
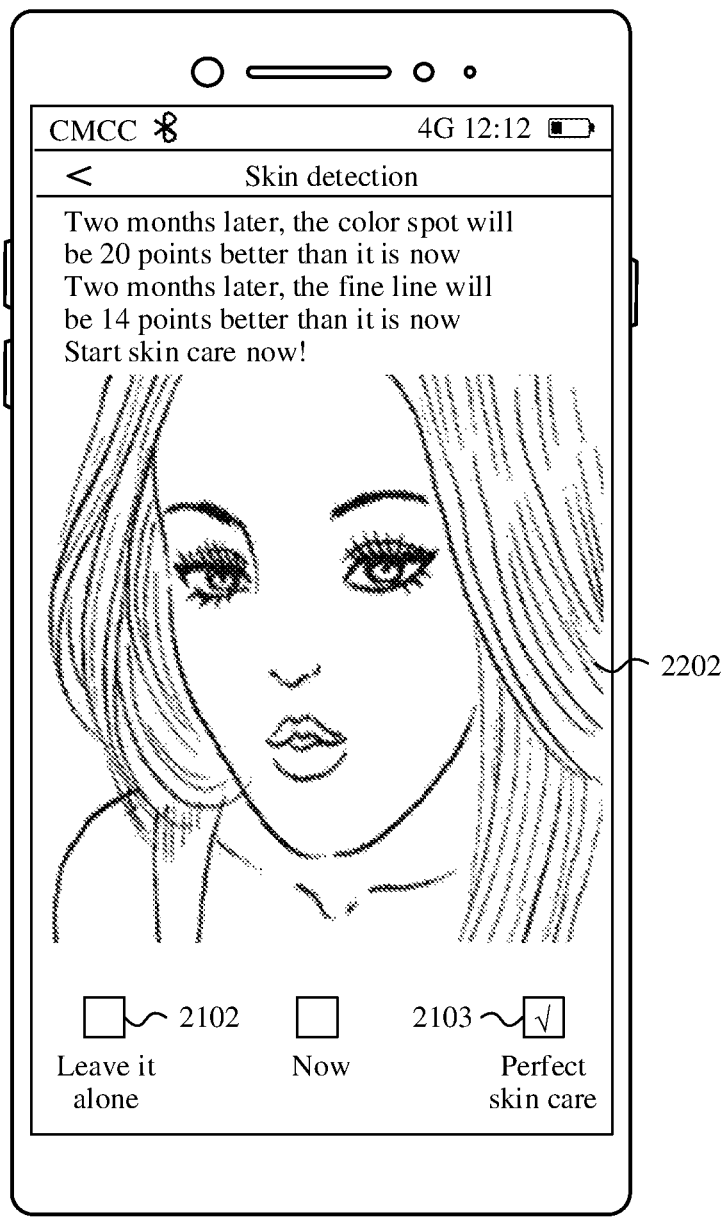

An aging button 2102 and a de-aging button 2103 may be further set in the interface 2101. If it is detected that the user taps the aging button 2102, as shown in FIG. 22(a), the mobile phone may simulate, by using the foregoing steps S404 and S1403, a face image 2201 obtained after the color spot problem and the fine line problem are aged. If it is detected that the user taps the de-aging button 2103, as shown in FIG. 22(b), the mobile phone may simulate, by using the foregoing steps S405 and S1404, a face image 2202 obtained after the color spot problem and the fine line problem are de-aged.

It can be learned that, in the skin detection method provided in this application, the mobile phone may simulate a change in aging/de-aging of a skin problem in a period of time for the detected skin problem (for example, the foregoing color spot problem or the fine line problem), and the mobile phone may display a simulated aged/de-aged face image to the user, so that the user can intuitively and vividly sense a change of the user's skin in a future period of time, thereby reminding the user to repair the skin problem in a timely manner, and improving user experience.

Figure 23:
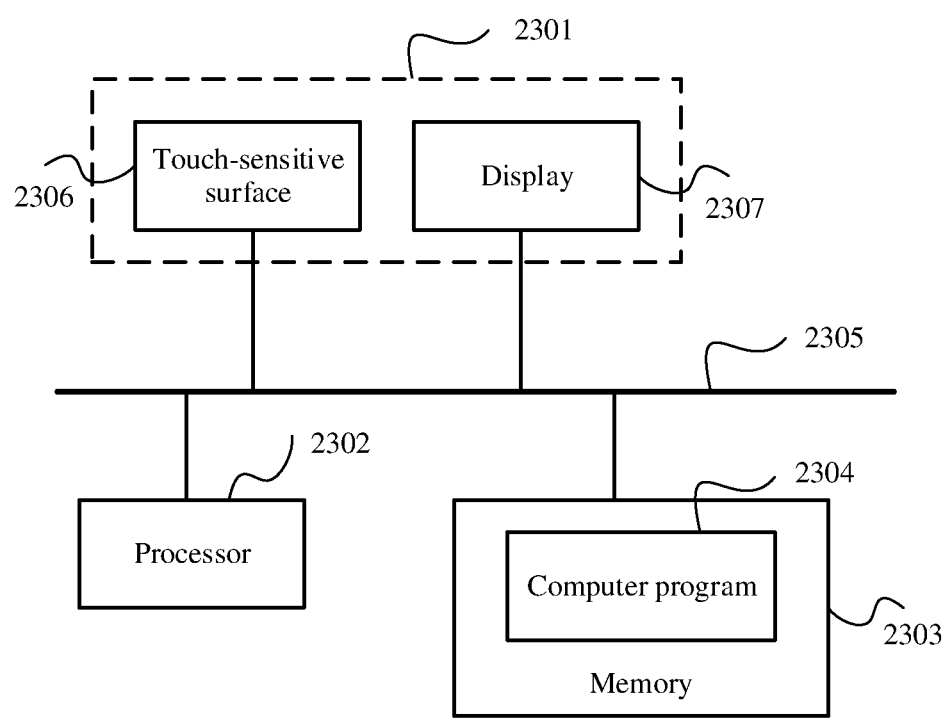
FIG. 23 is a schematic structural diagram 2 of an electronic device according to an embodiment of this application.

As shown in FIG. 23, an embodiment of this application discloses an electronic device, including a touchscreen 2301, where the touchscreen 2301 includes a touch-sensitive surface 2306 and a display 2307; one or more processors 2302; a memory 2303; one or more application programs (not shown); and one or more computer programs 2304. The foregoing devices may be connected through one or more communications buses 2305. The one or more computer programs 2304 are stored in the memory 2303 and are configured to be executed by the one or more processors 2302. The one or more computer programs 2304 include instructions, and the instructions may be used to perform the skin detection method in steps S401 to S405 or S1401 to S104 in the foregoing embodiments.

Based on the foregoing descriptions about implementations, a person skilled in the art may clearly understand that, for the purpose of convenient and brief description, only division into the foregoing function modules is used as an example for description. In actual application, the foregoing functions can be allocated to different function modules for implementation based on a requirement. In other words, an inner structure of an apparatus is divided into different function modules to implement all or some of the functions described above. For a detailed working process of the foregoing system, apparatus, and unit, refer to a corresponding process in the foregoing method embodiments. Details are not described herein again.

Function units in the embodiments of this application may be integrated into one processing unit, or each of the units may exist alone physically, or two or more units may be integrated into one unit. The integrated unit may be implemented in a form of hardware, or may be implemented in a form of a software function unit.

When the integrated unit is implemented in the form of a software function unit and sold or used as an independent product, the integrated unit may be stored in a computer readable storage medium. Based on such an understanding, the technical solutions of the embodiments of this application essentially, or the part contributing to the prior art, or all or some of the technical solutions may be implemented in the form of a software product. The computer software product is stored in a storage medium and includes several instructions for instructing a computer device (which may be a personal computer, a server, a network device, or the like) or a processor to perform all or some of the steps of the methods described in the embodiments of this application. The foregoing storage medium includes any medium that can store program code, such as a flash memory, a removable hard disk, a read-only memory, a random access memory, a magnetic disk, or an optical disc.

The foregoing descriptions are merely specific implementations of the embodiments of this application, but the protection scope of the embodiments of this application is not limited thereto. Any variation or replacement within the technical scope disclosed in the embodiments of this application shall fall within the protection scope of the embodiments of this application. Therefore, the protection scope of the embodiments of this application shall be subject to the protection scope of the claims.

What is claimed is:

1. A skin detection method, comprises:
   obtaining, by an electronic device, a face image of a user;
   detecting, by the electronic device, a skin problem that appears in the face image;
   prompting, by the electronic device in a first interface, the user that the skin problem appears on a face, wherein the first interface comprises the face image; and
   displaying, by the electronic device, a second interface in response to a selection performed by the user in the first interface, wherein the selection is a selection of a first aging operation or a second aging operation, wherein the second interface comprises a first facial simulated image obtained after the skin problem is aged; or
   displaying, by the electronic device, a third interface in response to the selection performed by the user in the first interface, wherein the selection is a selection of a first de-aging operation or a second de-aging operation, wherein the third interface comprises a second facial simulated image obtained after the skin problem is de-aged;
   wherein the method further comprises:
   (1) when the skin problem comprises a color spot problem and the selection is a selection of the first aging operation:
      detecting, by the electronic device in the face image, a color spot region in which the color spot problem appears;
      obtaining, by the electronic device, a change coefficient K1 of an L pixel channel, a change coefficient K2 of a pixel channel, and a change coefficient K3 of a b pixel channel in the color spot region;
      performing, by the electronic device, aging processing on the L pixel channel in the color spot region, to obtain a pixel value L' of an aged L pixel channel, wherein L'=L+K1×C1×L, L is a pixel value of the L pixel channel before the aging processing, and C1 is a constant;
      performing, by the electronic device, aging processing on the a pixel channel in the color spot region, to obtain a pixel value a' of an aged a pixel channel, wherein a'=a+K2×C2× a, a is a pixel value of the a pixel channel before the aging processing, and C2 is a constant; and
      performing, by the electronic device, aging processing on the b pixel channel in the color spot region, to obtain a pixel value b' of an aged b pixel channel, wherein b'=b+K3×C3×b, b is a pixel value of the b pixel channel before the aging processing, and C3 is a constant; or
   (2) when the skin problem comprises a color spot problem and the selection is a selection of the first de-aging operation:
      detecting, by the electronic device in the face image, a color spot region in which the color spot problem appears;
      obtaining, by the electronic device, a change coefficient K1 of an L pixel channel, a change coefficient K2 of a pixel channel, and a change coefficient K3 of a b pixel channel in the color spot region;
      performing, by the electronic device, de-aging processing on the L pixel channel in the color spot region, to obtain a pixel value L' of de-aged L pixel channel, wherein L'=L−K1×C1×L, L is a pixel value of the L pixel channel before the de-aging processing, and C1 is a constant;
      performing, by the electronic device, de-aging processing on the a pixel channel in the color spot region, to obtain a pixel value a' of a de-aged a pixel channel, wherein a'=a−K2×C2× a, a is a pixel value of the pixel channel before the de-aging processing, and C2 is a constant; and
      performing, by the electronic device, de-aging processing on the b pixel channel in the color spot region, to obtain a pixel value b' of a de-aged b pixel channel, wherein b'=b−K3×C3×b, b is a pixel value of the b pixel channel before the de-aging processing, and C3 is a constant; or
   (3) the skin problem comprises a fine line problem and the selection is a selection of the second aging operation:
      detecting, by the electronic device in the face image, a fine line region in which the fine line problem appears;
      obtaining, by the electronic device, a change coefficient D of the fine line region;
      performing, by the electronic device, aging processing on an R pixel channel in the fine line region, to obtain a pixel value R' of an aged R pixel channel, wherein R'=R+C5×D, R is a pixel value of the R pixel channel before the aging processing, and C5 is a constant;
      performing, by the electronic device, aging processing on a G pixel channel in the fine line region, to obtain a pixel value G' of an aged G pixel channel, wherein G'=G+C6×D, G is a pixel value of the G pixel channel before the aging processing, and C6 is a constant; and
      performing, by the electronic device, aging processing on a B pixel channel in the fine line region, to obtain a pixel value B' of an aged B pixel channel, wherein B'=B+C7×D, R is a pixel value of the B pixel channel before the aging processing, and C7 is a constant; or (4) the skin problem comprises a fine line problem and the selection is a selection of the second de-aging operation:

obtaining, by the electronic device, a change coefficient D of the fine line region in the face image;

performing, by the electronic device, de-aging processing on an R pixel channel in the fine line region, to obtain a pixel value R' of a de-aged R pixel channel, wherein R'=R−C5×D, R is a pixel value of the R pixel channel before the de-aging processing, and C5 is a constant;

performing, by the electronic device, de-aging processing on a G pixel channel in the fine line region, to obtain a pixel value G' of a de-aged G pixel channel, wherein G'=G−C6×D, R is a pixel value of the G pixel channel before the de-aging processing, and C6 is a constant and performing, by the electronic device, de-aging processing on a B pixel channel in the fine line region, to obtain a pixel value B' of a de-aged B pixel channel, wherein B'=B−C7×D, R is a pixel value of the B pixel channel before the de-aging processing, and C7 is a constant.

2. The method of claim 1, wherein the skin problem comprises the color spot problem, and wherein the selection is a selection of the first aging operation or the first de-aging operation.

3. The method of claim 1, wherein the skin problem comprises a fine line problem, and the selection is the second aging operation or the second de-aging operation.

4. The method of claim 1, wherein the first interface further comprises an aging progress bar and a slider, and the election includes a sliding operation of dragging the slider on the aging progress bar by the user; and the method further comprises:

displaying, by the electronic device in the second interface, the first facial simulated image corresponding to the first position, when the slider is dragged to a first position of the aging progress bar.

5. The method of claim 1, wherein the first interface further comprises a scoring status or a skin care suggestion for the skin problem in the face image.

6. An electronic device, comprising:
a non-transitory memory comprising instructions; and
a processor coupled to the non-transitory memory, the instructions being executed by the processor to cause the electronic device to:
obtain a face image of a user;
detect a skin problem that appears in the face image;
prompt in a first interface, the user that the skin problem appears on a face, wherein the first interface comprises the face image; and
display a second interface in response to a selection performed by the user in the first interface, wherein the selection is a selection of a first aging operation or a second aging operation, wherein the second interface comprises a first facial simulated image obtained after the skin problem is aged; or
display a third interface in response to the selection performed by the user in the first interface, wherein the selection is a selection of a first de-aging operation or a second de-aging operation, wherein the third interface comprises a second facial simulated image obtained after the skin problem is de-aged;

wherein the instructions being executed by the processor cause the electronic device further to:

(1) when the skin problem comprises a color spot problem and the selection is a selection of the first aging operation:
detect a color spot region in which the color spot problem appears;
obtain a change coefficient K1 of an L pixel channel, a change coefficient K2 of a pixel channel, and a change coefficient K3 of a b pixel channel in the color spot region;
perform aging processing on the L pixel channel in the color spot region, to obtain a pixel value L' of an aged L pixel channel, wherein L'=L+K1×C1×L, L is a pixel value of the L pixel channel before the aging processing, and C1 is a constant;
perform aging processing on the a pixel channel in the color spot region, to obtain a pixel value a' of an aged a pixel channel, wherein a'=a+K2×C2× a, a is a pixel value of the a pixel channel before the aging processing, and C2 is a constant; and
perform aging processing on the b pixel channel in the color spot region, to obtain a pixel value b' of an aged b pixel channel, wherein b'=b+K3×C3×b, b is a pixel value of the b pixel channel before the aging processing, and C3 is a constant; or (2) when the skin problem comprises a color spot problem and the selection is a selection of the first de-aging operation:
detect a color spot region in which the color spot problem appears;
obtain a change coefficient K1 of an L pixel channel, a change coefficient K2 of a pixel channel, and a change coefficient K3 of a b pixel channel in the color spot region;
perform de-aging processing on the L pixel channel in the color spot region, to obtain a pixel value L' of de-aged L pixel channel, wherein L'=L−K1×C1×L, L is a pixel value of the L pixel channel before the de-aging processing, and C1 is a constant;
perform de-aging processing on the a pixel channel in the color spot region, to obtain a pixel value a' of a de-aged a pixel channel, wherein a'=a−K2×C2× a, a is a pixel value of the pixel channel before the de-aging processing, and C2 is a constant; and
perform de-aging processing on the b pixel channel in the color spot region, to obtain a pixel value b' of a de-aged b pixel channel, wherein b'=b−K3×C3×b, b is a pixel value of the b pixel channel before the de-aging processing, and C3 is a constant; or (3) the skin problem comprises a fine line problem and the selection is a selection of the second aging operation:
detect a fine line region in which the fine line problem appears;
obtain a change coefficient D of the fine line region;
perform aging processing on an R pixel channel in the fine line region, to obtain a pixel value R' of an aged R pixel channel, wherein R'=R+C5×D, R is a pixel value of the R pixel channel before the aging processing, and C5 is a constant;
perform aging processing on a G pixel channel in the fine line region, to obtain a pixel value G' of an aged G pixel channel, wherein G'=G+C6×D, G is a pixel value of the G pixel channel before the aging processing, and C6 is a constant; and
perform aging processing on a B pixel channel in the fine line region, to obtain a pixel value B' of an aged B pixel channel, wherein $B'=B+C7\times D$, R is a pixel value of the B pixel channel before the aging processing, and C7 is a constant or (4) the skin problem comprises a fine line problem and the selection is a selection of the second de-aging operation:

obtain a change coefficient D of the fine line region in the face image;

perform de-aging processing on an R pixel channel in the fine line region, to obtain a pixel value R' of a de-aged R pixel channel, wherein $R'=R-C5\times D$, R is a pixel value of the R pixel channel before the de-aging processing, and C5 is a constant;

perform de-aging processing on a G pixel channel in the fine line region, to obtain a pixel value G' of a de-aged G pixel channel, wherein $G'=G-C6\times D$, G is a pixel value of the G pixel channel before the de-aging processing, and C6 is a constant; and perform de-aging processing on a B pixel channel in the fine line region, to obtain a pixel value B' of a de-aged B pixel channel, wherein $B'=B-C7\times D$, R is a pixel value of the B pixel channel before the de-aging processing, and C7 is a constant.

7. The electronic device of claim 6, wherein the skin problem comprises a color spot problem, and wherein the selection is a selection of the first aging operation or the first de-aging operation.

8. The electronic device of claim 6, wherein the skin problem comprises the fine line problem, and wherein the selection is a selection of the first aging operation or the first de-aging operation.

9. The electronic device of claim 6, wherein the first interface further comprises an aging progress bar and a slider, and the selection includes a sliding operation of dragging the slider on the aging progress bar by the user; the instructions further cause the electronic device to:

display in the second interface, the first facial simulated image corresponding to the first position, when the slider is dragged to a first position of the aging progress bar.

10. The electronic device of claim 6, wherein the first interface further comprises a scoring status or a skin care suggestion for the skin problem in the face image.

* * * * *

UNITED STATES PATENT AND TRADEMARK OFFICE
CERTIFICATE OF CORRECTION

PATENT NO. : 11,759,143 B2
APPLICATION NO. : 17/418368
DATED : September 19, 2023
INVENTOR(S) : Zhizhi Guo et al.

It is certified that error appears in the above-identified patent and that said Letters Patent is hereby corrected as shown below:

On the Title Page

Change item (71) Applicant: "HONOR DEVICE CO., LTD., Guangdong (CN)", to "HONOR DEVICE CO., LTD., Shenzhen (CN)"

Item (72) Inventors: "Zhizhi Guo, Guangdong (CN)" should be "(72) Inventors: Zhizhi Guo, Shenzhen (CN)"
"Hongwei Hu, Guangdong (CN)" should be "Hongwei Hu, Shenzhen (CN)"
"Wenmei Gao, Guangdong (CN)" should be "Wenmei Gao, Shenzhen (CN)"
"Chen Dong, Guangdong (CN)" should be "Chen Dong, Shenzhen (CN)"

Item (73) Assignee: "HONOR DEVICE CO., LTD., Guangdong (CN)" should be "HONOR DEVICE CO., LTD., Shenzhen (CN)"

Signed and Sealed this
Second Day of January, 2024

Katherine Kelly Vidal
*Director of the United States Patent and Trademark Office*